US010634669B2

United States Patent
Liu et al.

(10) Patent No.: US 10,634,669 B2
(45) Date of Patent: *Apr. 28, 2020

(54) METHODS AND ANTIBODIES FOR DESIGNING AND DETECTING MUTATION-SPECIFIC OR HIDDEN EPITOPE/ANTIGENA

(71) Applicants: Chunli Liu, Baltimore, MD (US); Bingren Hu, Baltimore, MD (US)

(72) Inventors: Chunli Liu, Baltimore, MD (US); Bingren Hu, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/236,509

(22) Filed: Aug. 15, 2016

(65) Prior Publication Data

US 2018/0017549 A1   Jan. 18, 2018

Related U.S. Application Data

(63) Continuation-in-part of application No. 13/312,285, filed on Dec. 6, 2011, now Pat. No. 9,383,367.

(Continued)

(51) Int. Cl.
| | | |
|---|---|---|
| *G01N 33/53* | (2006.01) | |
| *C07K 16/18* | (2006.01) | |
| *C12Q 1/37* | (2006.01) | |
| *G01N 33/68* | (2006.01) | |
| *C07K 16/00* | (2006.01) | |

(52) U.S. Cl.
CPC ......... *G01N 33/5306* (2013.01); *C07K 16/00* (2013.01); *C07K 16/18* (2013.01); *C12Q 1/37* (2013.01); *G01N 33/6878* (2013.01); *C07K 2317/24* (2013.01); *C07K 2317/34* (2013.01); *C07K 2317/569* (2013.01)

(58) Field of Classification Search
None
See application file for complete search history.

(56) References Cited

U.S. PATENT DOCUMENTS

| 9,383,367 B1 * | 7/2016 | Liu | G01N 33/6878 |
| 9,606,125 B2 * | 3/2017 | Liu | G01N 33/6878 |
| 9,606,128 B2 * | 3/2017 | Liu | G01N 33/6878 |

OTHER PUBLICATIONS

Kirkpatrick et al. Quantitative analysis of in vitro ubiquitinated cyclin B1 reveals compex chain topology. Nature Cell Biol. 2006, vol. 8, No. 7, pp. 700-710 and supporting online material. (Year: 2006).*

(Continued)

*Primary Examiner* — Shafiqul Haq

(57) ABSTRACT

This invention discloses "Artificially Cleaved Epitope (ACE)" methods, antibodies, reagents, immunoassays, and kits for designing and detecting mutation-specific epitopes/antigens. The ACE methods can detect epitopes that are either absent or poorly recognizable or accessible naturally to antibodies, and thus must be specifically and artificially created (free terminals) and/or exposed in samples and sample preparations for antibody detection. The ACE methods comprise ACE antigen design and ACE antigen detection. The ACE methods, antibodies, reagents, immunoassays, and kits are useful in research and discovery, diagnostic, and therapeutic applications. In another aspect, the ACE methods can artificially and specifically expose hidden antigens while reducing the antibody non-specific bindings in all antibody-based applications.

Figure 1A:
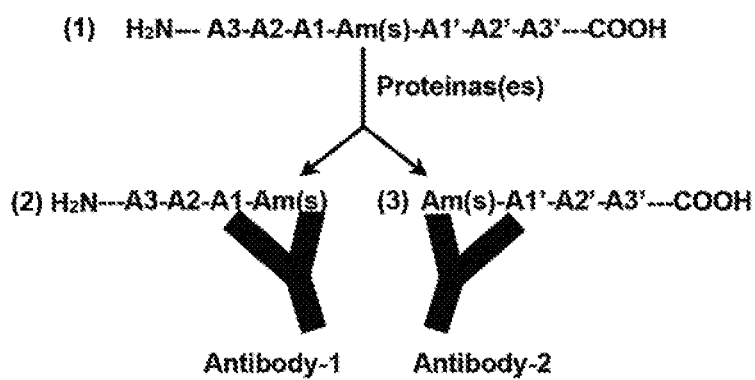

10 Claims, 17 Drawing Sheets
Specification includes a Sequence Listing.

Related U.S. Application Data

(60) Provisional application No. 62/209,774, filed on Aug. 25, 2015.

(56) References Cited

OTHER PUBLICATIONS

Koivunen et al. Principles of immunochemical techniques used in clinical laboratories. LABMEDICINE 2006, Vo.37, No. 8, pp. 490-497. (Year: 2006).*

Wang et al. Analysis of nondegradative protein ubiquitylation with a monoclonal antibody specific for lysine-63-linked polyubiquitin. PNAS 2008, vol. 105, No. 51, pp. 20197-20202. (Year: 2008).*

Dvorak et al. Immunohistochemistry with the anti-BRAF V600E (VE1) antibody: impact of pre-analytical conditions and concordance with DNA sequencing in colorectal and papillary thyroid carcinoma. Pathology 2014, vol. 46, No. 6, pp. 509-517. (Year: 2014).*

* cited by examiner

Fig. 7A

| Gene Name | Mutation Site | Mutation Type | Related Disease |
|---|---|---|---|
| GNA11 | p.Q209P | missense | melanoma |
| GNA11 | p.Q209L | missense | melanoma |
| ESR1 | p.E380Q | missense | breast cancer |
| ESR1 | p.S463P | missense | progesterone-receptor positive breast cancer |
| ESR1 | p.V534E | missense | progesterone-receptor positive breast cancer |
| ESR1 | p.P535H | missense | progesterone-receptor positive breast cancer |
| ESR1 | p.L536R | missense | progesterone-receptor positive breast cancer |
| ESR1 | p.Y537N | missense | progesterone-receptor positive breast cancer |
| ESR1 | p.Y537S | missense | progesterone-receptor positive breast cancer |
| ESR1 | p.Y537C | missense | progesterone-receptor positive breast cancer |
| ESR1 | p.D538G | missense | progesterone-receptor positive breast cancer |
| PIK3R2 | p.N561D | missense | endometrial cancer |
| SMO | p.D473H | missense | medulloblastoma |
| KRAS | p.Q61K | missense | colorectal cancer |
| KRAS | p.Q61L | missense | thyroid cancer |
| KRAS | p.Q61R | missense | colorectal cancer |
| KRAS | p.Q61P | missense | thyroid cancer |
| KRAS | p.Q61H | missense | colorectal cancer |
| KRAS | p.Q61H | missense | colorectal cancer |
| KRAS | p.G12C | missense | colorectal cancer |
| KRAS | p.G12R | missense | non-small cell lung carcinoma |
| KRAS | p.G12S | missense | non-small cell lung carcinoma |
| KRAS | p.K117N | missense | colorectal cancer |
| KRAS | p.K117N | missense | colorectal cancer |
| KRAS | p.G12V | missense | acute myeloid leukemia |
| KRAS | p.G12A | missense | colorectal cancer |
| KRAS | p.G12D | missense | thyroid cancer |
| KRAS | p.G13C | missense | colorectal cancer |
| KRAS | p.G13R | missense | colorectal cancer |
| KRAS | p.G13S | missense | colorectal cancer |
| KRAS | p.G13V | missense | colorectal cancer |
| KRAS | p.G13A | missense | colorectal cancer |
| KRAS | p.G13D | missense | non-small cell lung carcinoma |
| KRAS | p.A146P | missense | colorectal cancer |
| KRAS | p.A146T | missense | colorectal cancer |
| KRAS | p.A146V | missense | colorectal cancer |
| PDGFRA | p.V561D | missense | gastrointestinal stromal tumor |
| PDGFRA | p.P577S | missense | melanoma |
| PDGFRA | p.V658A | missense | melanoma |
| PDGFRA | p.N659K | missense | gastrointestinal stromal tumor |
| PDGFRA | p.N659K | missense | gastrointestinal stromal tumor |
| PDGFRA | p.R841K | missense | melanoma |
| PDGFRA | p.D842V | missense | gastrointestinal stromal tumor |

Fig. 7B

| Gene Name | Mutation Site | Mutation Type | Related Disease |
|---|---|---|---|
| PDGFRA | p.H845Y | missense | melanoma |
| PDGFRA | p.G853D | missense | melanoma |
| HERC2 | p.L755S | missense | breast cancer |
| HERC2 | p.DTKH759in_frame_delEPNT | in_frame_del | breast cancer |
| HERC2 | p.A309G | missense | breast cancer |
| MAP2K2 | p.V35M | missense | melanoma |
| MAP2K2 | p.L46F | missense | melanoma |
| MAP2K2 | p.Q60P | missense | melanoma |
| MAP2K2 | p.C125S | missense | melanoma |
| MAP2K2 | p.N126D | missense | melanoma |
| PIK3CA | p.E542K | missense | ovarian cancer |
| PIK3CA | p.E545K | missense | non-small cell lung carcinoma |
| PIK3CA | p.E545Q | missense | non-small cell lung carcinoma |
| PIK3CA | p.E545A | missense | colorectal cancer |
| PIK3CA | p.E545G | missense | colorectal cancer |
| PIK3CA | p.E545V | missense | breast cancer |
| PIK3CA | p.Q546K | missense | breast cancer |
| PIK3CA | p.Q546E | missense | colorectal cancer |
| PIK3CA | p.Q546P | missense | breast cancer |
| PIK3CA | p.Q546R | missense | breast cancer |
| PIK3CA | p.Q546L | missense | breast cancer |
| PIK3CA | p.D549N | missense | colorectal cancer |
| PIK3CA | p.H1047R | missense | non-small cell lung carcinoma |
| PIK3CA | p.H1047L | missense | breast cancer |
| CBL | p.Y371H | missense | hematologic cancer |
| CBL | p.C384R | missense | hematologic cancer |
| DNMT3A | p.R882C | missense | acute myeloid leukemia |
| DNMT3A | p.R882G | missense | acute myeloid leukemia |
| DNMT3A | p.R882S | missense | acute myeloid leukemia |
| DNMT3A | p.R882L | missense | acute myeloid leukemia |
| DNMT3A | p.R882P | missense | acute myeloid leukemia |
| DNMT3A | p.R882H | missense | acute myeloid leukemia |
| ERBB3 | p.Q809R | missense | cancer |
| ERBB3 | p.P262H | missense | cancer |
| ERBB3 | p.G284R | missense | colon cancer |
| TP53 | p.V173G | missense | acute myeloid leukemia |
| TP53 | p.V173A | missense | acute myeloid leukemia |
| TP53 | p.Y220C | missense | acute myeloid leukemia |
| TP53 | p.R248Q | missense | acute myeloid leukemia |
| TP53 | p.R249W | missense | acute myeloid leukemia |
| TP53 | p.R249T | missense | acute myeloid leukemia |

Fig. 7C

| Gene Name | Mutation Site | Mutation Type | Related Disease |
|---|---|---|---|
| TP53 | p.R273C | missense | acute myeloid leukemia |
| TP53 | p.R273H | missense | acute myeloid leukemia |
| ERBB2 | p.LREN755in_frame_del* | in_frame_del | breast cancer |
| ERBB2 | p.D769H | missense | breast cancer |
| ERBB2 | p.D769Y | missense | breast cancer |
| ERBB2 | p.V777L | missense | breast cancer |
| ERBB2 | p.779in_frame_insLPS | in_frame_ins | breast cancer |
| ERBB2 | p.V842I | missense | breast cancer |
| ERBB2 | p.R896C | missense | breast cancer |
| ERBB2 | p.G309E | missense | lung adenocarcinoma |
| ERBB2 | p.G309A | missense | breast cancer |
| ERBB2 | p.S310Y | missense | cancer |
| ERBB2 | p.S310F | missense | cancer |
| EGFR | p.S492G | missense | colorectal cancer |
| EGFR | p.P546S | missense | cancer |
| EGFR | p.G598V | missense | brain cancer |
| EGFR | p.E690K | missense | endometrial cancer |
| EGFR | p.G719S | missense | non-small cell lung carcinoma |
| EGFR | p.G719C | missense | non-small cell lung carcinoma |
| EGFR | p.G719D | missense | lung squamous cell carcinoma |
| EGFR | p.G719A | missense | non-small cell lung carcinoma |
| EGFR | p.L747S | missense | lung squamous cell carcinoma |
| EGFR | p.P753S | missense | cancer |
| EGFR | p.S768I | missense | lung squamous cell carcinoma |
| EGFR | p.T790M | missense | non-small cell lung carcinoma |
| EGFR | p.V843I | missense | cancer |
| EGFR | p.L858R | missense | non-small cell lung carcinoma |
| EGFR | p.L861Q | missense | non-small cell lung carcinoma |
| EGFR | p.L861P | missense | lung squamous cell carcinoma |
| EGFR | p.L861R | missense | lung squamous cell carcinoma |
| EGFR | p.R108K | missense | brain cancer |
| EGFR | p.T263P | missense | brain cancer |
| EGFR | p.A289V | missense | brain cancer |
| CSF1R | p.Y571D | missense | hematologic cancer |
| GNAQ | p.Q209L | missense | melanoma |
| GNAQ | p.Q209R | missense | melanoma |
| GNAQ | p.Q209P | missense | melanoma |
| KIT | p.E490K | missense | thymic carcinoma |
| KIT | p.F504L | missense | melanoma |
| KIT | p.K550N | missense | melanoma |
| KIT | p.K550N | missense | melanoma |

Fig. 7D

| Gene Name | Mutation Site | Mutation Type | Related Disease |
|---|---|---|---|
| KIT | p.Y553N | missense | melanoma |
| KIT | p.W557R | missense | melanoma |
| KIT | p.W557R | missense | melanoma |
| KIT | p.K558N | missense | melanoma |
| KIT | p.K558N | missense | melanoma |
| KIT | p.V559I | missense | gastrointestinal stromal tumor |
| KIT | p.V559D | missense | gastrointestinal stromal tumor |
| KIT | p.V559A | missense | melanoma |
| KIT | p.V559G | missense | melanoma |
| KIT | p.VEEI560in_frame_delLRR | in_frame_del | thymic carcinoma |
| KIT | p.V560D | missense | melanoma |
| KIT | p.V560A | missense | melanoma |
| KIT | p.V560G | missense | melanoma |
| KIT | p.N566D | missense | melanoma |
| KIT | p.V569G | missense | melanoma |
| KIT | p.L576P | missense | melanoma |
| KIT | p.PYDH577in_frame_delLMIT | in_frame_del | thymic carcinoma |
| KIT | p.K642E | missense | melanoma |
| KIT | p.V654E | missense | melanoma |
| KIT | p.V654A | missense | gastrointestinal stromal tumor |
| KIT | p.N655S | missense | melanoma |
| KIT | p.N655K | missense | melanoma |
| KIT | p.N655K | missense | melanoma |
| KIT | p.T670I | missense | gastrointestinal stromal tumor |
| KIT | p.H697Y | missense | thymic carcinoma |
| KIT | p.D816H | missense | melanoma |
| KIT | p.D816Y | missense | acute myeloid leukemia |
| KIT | p.D816I | missense | acute myeloid leukemia |
| KIT | p.D816V | missense | acute myeloid leukemia |
| KIT | p.D820H | missense | melanoma |
| KIT | p.D820Y | missense | melanoma |
| KIT | p.D820V | missense | systemic mastocytosis |
| KIT | p.D820E | missense | thymic carcinoma |
| KIT | p.N822I | missense | gastrointestinal stromal tumor |
| KIT | p.N822K | missense | acute myeloid leukemia |
| KIT | p.N822K | missense | acute myeloid leukemia |
| KIT | p.Y823D | missense | gastrointestinal stromal tumor |
| KIT | p.A829P | missense | gastrointestinal stromal tumor |
| BRAF | p.G466V | missense | lung cancer |

Fig. 7E

| Gene Name | Mutation Site | Mutation Type | Related Disease |
|---|---|---|---|
| BRAF | p.G469A | missense | lung cancer |
| BRAF | p.G469E | missense | colorectal cancer |
| BRAF | p.Y472C | missense | lung cancer |
| BRAF | p.D594H | missense | melanoma |
| BRAF | p.D594N | missense | melanoma |
| BRAF | p.D594N | missense | melanoma |
| BRAF | p.D594V | missense | melanoma |
| BRAF | p.D594G | missense | melanoma |
| BRAF | p.D594A | missense | melanoma |
| BRAF | p.D594E | missense | melanoma |
| BRAF | p.D594E | missense | melanoma |
| BRAF | p.G596R | missense | colorectal cancer |
| BRAF | p.L597V | missense | melanoma |
| BRAF | p.L597R | missense | ovarian cancer |
| BRAF | p.L597Q | missense | melanoma |
| BRAF | p.L597S | missense | melanoma |
| BRAF | p.V600L | missense | melanoma |
| BRAF | p.V600M | missense | melanoma |
| BRAF | p.V600G | missense | melanoma |
| BRAF | p.V600E | missense | myeloma |
| BRAF | p.V600R | missense | melanoma |
| BRAF | p.V600K | missense | melanoma |
| BRAF | p.V600D | missense | melanoma |
| BRAF | p.K601E | missense | melanoma |
| BRAF | p.K601R | missense | melanoma |
| U2AF1 | p.S34F | missense | acute myeloid leukemia |
| U2AF1 | p.S34Y | missense | acute myeloid leukemia |
| U2AF1 | p.Q157R | missense | acute myeloid leukemia |
| U2AF1 | p.Q157P | missense | acute myeloid leukemia |
| FGFR4 | p.N535K | missense | rhabdomyosarcoma |
| FGFR4 | p.N535K | missense | rhabdomyosarcoma |
| FGFR4 | p.V550E | missense | rhabdomyosarcoma |
| NPM1 | p.W288fs | frame_shift_ins | acute myeloid leukemia |
| NPM1 | p.W288fs | frame_shift_ins | acute myeloid leukemia |
| NPM1 | p.W288fs | frame_shift_ins | acute myeloid leukemia |
| NPM1 | p.W288fs | frame_shift_ins | acute myeloid leukemia |
| RUNX1 | p.R162G | missense | acute myeloid leukemia |
| RUNX1 | p.R162K | missense | acute myeloid leukemia |
| RUNX1 | p.R162S | missense | acute myeloid leukemia |
| RUNX1 | p.R162S | missense | acute myeloid leukemia |
| RUNX1 | p.R201* | nonsense | acute myeloid leukemia |
| IL7R | p.S185C | missense | lymphoblastic leukemia |
| MAP2K1 | p.N382H | missense | melanoma |

Fig. 7F

| Gene Name | Mutation Site | Mutation Type | Related Disease |
|---|---|---|---|
| MAP2K1 | p.F53L | missense | melanoma |
| MAP2K1 | p.Q56P | missense | non-small cell lung carcinoma |
| MAP2K1 | p.K57E | missense | melanoma |
| MAP2K1 | p.K57N | missense | melanoma |
| MAP2K1 | p.K57N | missense | non-small cell lung carcinoma |
| MAP2K1 | p.D67N | missense | non-small cell lung carcinoma |
| MAP2K1 | p.I99T | missense | cancer |
| MAP2K1 | p.I103N | missense | cancer |
| MAP2K1 | p.I111N | missense | cancer |
| MAP2K1 | p.I111S | missense | melanoma |
| MAP2K1 | p.H119P | missense | cancer |
| MAP2K1 | p.E120D | missense | cancer |
| MAP2K1 | p.E120D | missense | cancer |
| MAP2K1 | p.C121S | missense | melanoma |
| MAP2K1 | p.P124S | missense | melanoma |
| MAP2K1 | p.P124L | missense | melanoma |
| MAP2K1 | p.G128D | missense | melanoma |
| MAP2K1 | p.F129L | missense | melanoma |
| MAP2K1 | p.E203K | missense | melanoma |
| MAP2K1 | p.V211D | missense | cancer |
| MAP2K1 | p.L215P | missense | cancer |
| MAP2K1 | p.P264S | missense | melanoma |
| BTK | p.C481S | missense | breast cancer |
| BTK | p.C481S | missense | breast cancer |
| HRAS | p.Q61R | missense | thyroid cancer |
| HRAS | p.G12R | missense | thyroid cancer |
| HRAS | p.G12V | missense | thyroid cancer |
| HRAS | p.G13C | missense | thyroid cancer |
| HRAS | p.G13R | missense | thyroid cancer |
| MET | p.R988C | missense | cancer |
| MET | p.T1010I | missense | cancer |
| MET | p.V1110I | missense | cancer |
| MET | p.H1112R | missense | renal carcinoma |
| MET | p.Y1248C | missense | cancer |
| MET | p.Y1253D | missense | cancer |
| MET | p.M1268T | missense | renal carcinoma |
| MET | p.M1268I | missense | cancer |
| MET | p.M1268I | missense | cancer |
| MET | p.M1268I | missense | cancer |
| EZH2 | p.Y646H | missense | lymphoma |
| EZH2 | p.Y646N | missense | lymphoma |
| EZH2 | p.Y646F | missense | lymphoma |
| EZH2 | p.Y646S | missense | lymphoma |

Fig. 7G

| Gene Name | Mutation Site | Mutation Type | Related Disease |
|---|---|---|---|
| EZH2 | p.A682G | missense | lymphoma |
| STK11 | p.D194E | missense | rhabdomyosarcoma |
| STK11 | p.D194E | missense | rhabdomyosarcoma |
| IDH2 | p.R140W | missense | acute myeloid leukemia |
| IDH2 | p.R140L | missense | acute myeloid leukemia |
| IDH2 | p.R140Q | missense | acute myeloid leukemia |
| IDH2 | p.R172M | missense | acute myeloid leukemia |
| IDH2 | p.R172K | missense | acute myeloid leukemia |
| IDH2 | p.R172S | missense | acute myeloid leukemia |
| WT1 | p.A382fs | frame_shift_ins | acute myeloid leukemia |
| SF3B1 | p.K666E | missense | acute myeloid leukemia |
| SF3B1 | p.K666R | missense | acute myeloid leukemia |
| SF3B1 | p.K666T | missense | acute myeloid leukemia |
| SF3B1 | p.K666N | missense | acute myeloid leukemia |
| SF3B1 | p.K666N | missense | acute myeloid leukemia |
| SF3B1 | p.K700* | nonsense | acute myeloid leukemia |
| SF3B1 | p.K700E | missense | acute myeloid leukemia |
| SF3B1 | p.K700Q | missense | acute myeloid leukemia |
| SF3B1 | p.K700I | missense | acute myeloid leukemia |
| SF3B1 | p.K700R | missense | acute myeloid leukemia |
| SF3B1 | p.K700T | missense | acute myeloid leukemia |
| SF3B1 | p.K700N | missense | acute myeloid leukemia |
| SF3B1 | p.K700N | missense | acute myeloid leukemia |
| FGFR3 | p.Y375C | missense | myeloma |
| FGFR3 | p.V555M | missense | myeloma |
| GATA2 | p.T354M | missense | acute myeloid leukemia |
| GATA2 | p.R398W | missense | acute myeloid leukemia |
| JAK1 | p.S646F | missense | lymphoblastic leukemia |
| ERBB4 | p.R393W | missense | melanoma |
| ERBB4 | p.E452K | missense | melanoma |
| ERBB4 | p.E542K | missense | melanoma |
| ERBB4 | p.R544W | missense | melanoma |
| ERBB4 | p.E872K | missense | melanoma |
| ERBB4 | p.E317K | missense | melanoma |
| SMAD4 | p.D351N | missense | colorectal cancer |
| SMAD4 | p.D351H | missense | colorectal cancer |
| SMAD4 | p.D355E | missense | colorectal cancer |
| SMAD4 | p.R361S | missense | colorectal cancer |
| SMAD4 | p.R361C | missense | colorectal cancer |
| SMAD4 | p.R361H | missense | colorectal cancer |
| SMAD4 | p.D537Y | missense | colorectal cancer |
| SMAD4 | p.E330A | missense | colorectal cancer |
| IDH1 | p.R132C | missense | acute myeloid leukemia |

Fig. 7H

| Gene Name | Mutation Site | Mutation Type | Related Disease |
|---|---|---|---|
| IDH1 | p.R132G | missense | acute myeloid leukemia |
| IDH1 | p.R132S | missense | acute myeloid leukemia |
| IDH1 | p.R132L | missense | acute myeloid leukemia |
| IDH1 | p.R132P | missense | acute myeloid leukemia |
| IDH1 | p.R132H | missense | acute myeloid leukemia |
| AKT1 | p.Q79K | missense | melanoma |
| AKT1 | p.E17K | missense | colorectal cancer |
| CTNNB1 | p.S37Y | missense | melanoma |
| CTNNB1 | p.S37F | missense | melanoma |
| CTNNB1 | p.S45P | missense | melanoma |
| CTNNB1 | p.S45Y | missense | melanoma |
| CTNNB1 | p.S45F | missense | melanoma |
| GNAS | p.R202C | missense | cancer |
| GNAS | p.R202H | missense | cancer |
| GNAS | p.R202L | missense | cancer |
| RET | p.C634W | missense | thyroid cancer |
| RET | p.M918T | missense | thyroid cancer |
| EPHA2 | p.G391R | missense | lung squamous cell carcinoma |
| EPHA2 | p.G391R | missense | lung squamous cell carcinoma |
| PLCG2 | p.R665W | missense | breast cancer |
| PLCG2 | p.L845F | missense | breast cancer |
| PLCG2 | p.L845F | missense | breast cancer |
| MTOR | p.L1460P | missense | renal carcinoma |
| MTOR | p.E2014K | missense | bladder transitional cell carcinoma |
| MTOR | p.S2215Y | missense | renal carcinoma |
| MTOR | p.Q2223K | missense | renal carcinoma |
| MTOR | p.E2419K | missense | bladder transitional cell carcinoma |
| MTOR | p.R2505P | missense | renal carcinoma |
| DDR2 | p.G505S | missense | lung squamous cell carcinoma |
| DDR2 | p.L63V | missense | lung squamous cell carcinoma |
| DDR2 | p.I638F | missense | lung squamous cell carcinoma |
| DDR2 | p.S768R | missense | squamous cell carcinoma |
| DDR2 | p.G774V | missense | lung squamous cell carcinoma |
| DDR2 | p.L239R | missense | lung squamous cell carcinoma |
| DDR2 | p.G253C | missense | lung squamous cell carcinoma |
| ROS1 | p.G2032R | missense | lung adenocarcinoma |
| NRAS | p.Q61* | nonsense | non-small cell lung carcinoma |
| NRAS | p.Q61E | missense | melanoma |
| NRAS | p.Q61K | missense | colorectal cancer |
| NRAS | p.Q61L | missense | melanoma |
| NRAS | p.Q61R | missense | melanoma |
| NRAS | p.Q61P | missense | melanoma |
| NRAS | p.Q61H | missense | melanoma |

Fig. 7I

| Gene Name | Mutation Site | Mutation Type | Related Disease |
|---|---|---|---|
| NRAS | p.Q61H | missense | melanoma |
| NRAS | p.Q61L | missense | melanoma |
| NRAS | p.Q61R | missense | melanoma |
| NRAS | p.G12C | missense | melanoma |
| NRAS | p.G12R | missense | non-small cell lung carcinoma |
| NRAS | p.G12S | missense | melanoma |
| NRAS | p.G12V | missense | colorectal cancer |
| NRAS | p.G12A | missense | colorectal cancer |
| NRAS | p.G12D | missense | melanoma |
| NRAS | p.G13C | missense | melanoma |
| NRAS | p.G13R | missense | melanoma |
| NRAS | p.G13V | missense | melanoma |
| NRAS | p.G13A | missense | melanoma |
| NRAS | p.G13D | missense | melanoma |
| PTEN | p.R130G | missense | ovarian cancer |
| PTEN | p.R130* | nonsense | ovarian cancer |
| PTEN | p.R130Q | missense | ovarian cancer |
| PTEN | p.R159S | missense | colorectal cancer |
| PTEN | p.R233* | nonsense | colorectal cancer |
| PTEN | p.K267fs | frame_shift_del | colorectal cancer |
| ABL1 | p.T334A | missense | chronic myeloid leukemia |
| ABL1 | p.T334I | missense | chronic myeloid leukemia |
| ABL1 | p.F336I | missense | chronic myeloid leukemia |
| ABL1 | p.F336V | missense | chronic myeloid leukemia |
| ABL1 | p.F336C | missense | chronic myeloid leukemia |
| ABL1 | p.F336L | missense | chronic myeloid leukemia |
| ABL1 | p.F336L | missense | chronic myeloid leukemia |
| ABL1 | p.F378I | missense | chronic myeloid leukemia |
| ABL1 | p.F378L | missense | chronic myeloid leukemia |
| ABL1 | p.F378C | missense | chronic myeloid leukemia |
| ABL1 | p.E255K | missense | chronic myeloid leukemia |
| ABL1 | p.Y272H | missense | chronic myeloid leukemia |
| ABL1 | p.V318L | missense | chronic myeloid leukemia |
| MPL | p.W515L | missense | hematologic cancer |
| CSF3R | p.T615A | missense | chronic myeloid leukemia |
| CSF3R | p.T618I | missense | acute myeloid leukemia |
| ARAF | p.S214C | missense | lung adenocarcinoma |
| FLT3 | p.G619C | missense | acute myeloid leukemia |
| FLT3 | p.D651G | missense | acute myeloid leukemia |
| FLT3 | p.N676D | missense | acute myeloid leukemia |
| FLT3 | p.N676K | missense | acute myeloid leukemia |
| FLT3 | p.N676K | missense | acute myeloid leukemia |
| FLT3 | p.I687F | missense | acute myeloid leukemia |

Fig. 7J

| Gene Name | Mutation Site | Mutation Type | Related Disease |
|---|---|---|---|
| FLT3 | p.F691L | missense | acute myeloid leukemia |
| FLT3 | p.F691L | missense | acute myeloid leukemia |
| FLT3 | p.D835Y | missense | acute myeloid leukemia |
| FLT3 | p.D835H | missense | acute myeloid leukemia |
| FLT3 | p.D835N | missense | acute myeloid leukemia |
| FLT3 | p.D835V | missense | acute myeloid leukemia |
| FLT3 | p.D835A | missense | acute myeloid leukemia |
| FLT3 | p.D835F | missense | acute myeloid leukemia |
| FLT3 | p.D835E | missense | acute myeloid leukemia |
| FLT3 | p.D835E | missense | acute myeloid leukemia |
| FLT3 | p.I836L | missense | acute myeloid leukemia |
| FLT3 | p.I836M | missense | acute myeloid leukemia |
| FLT3 | p.D839G | missense | acute myeloid leukemia |
| FLT3 | p.Y842H | missense | acute myeloid leukemia |
| FLT3 | p.Y842C | missense | acute myeloid leukemia |
| CRLF2 | p.F232C | missense | lymphoblastic leukemia |
| JAK2 | p.V617F | missense | acute myeloid leukemia |
| JAK2 | p.R683G | missense | lymphoblastic leukemia |
| JAK2 | p.R683T | missense | lymphoblastic leukemia |
| JAK2 | p.R683S | missense | lymphoblastic leukemia |
| JAK2 | p.R683S | missense | lymphoblastic leukemia |
| ALK | p.D1091N | missense | neuroblastoma |
| ALK | p.G1128A | missense | brain cancer |
| ALK | p.T1151M | missense | neuroblastoma |
| ALK | p.L1152R | missense | lung adenocarcinoma |
| ALK | p.I1171N | missense | neuroblastoma |
| ALK | p.F1174V | missense | neuroblastoma |
| ALK | p.F1174I | missense | neuroblastoma |
| ALK | p.F1174C | missense | neuroblastoma |
| ALK | p.F1174L | missense | lung adenocarcinoma |
| ALK | p.F1174L | missense | neuroblastoma |
| ALK | p.R1192P | missense | brain cancer |
| ALK | p.L1196M | missense | lung adenocarcinoma |
| ALK | p.G1202R | missense | lung adenocarcinoma |
| ALK | p.S1206Y | missense | lung adenocarcinoma |
| ALK | p.D1225N | missense | rhabdomyosarcoma |
| ALK | p.F1245V | missense | neuroblastoma |
| ALK | p.F1245C | missense | neuroblastoma |
| ALK | p.F1245L | missense | neuroblastoma |
| ALK | p.G1269A | missense | lung adenocarcinoma |
| ALK | p.R1275Q | missense | neuroblastoma |
| ALK | p.Y1278S | missense | neuroblastoma |
| MYD88 | p.L273P | missense | lymphoma |

Fig. 7K

| Gene Name | Mutation Site | Mutation Type | Related Disease |
|---|---|---|---|
| RAF1 | p.W388S | missense | melanoma |
| RAF1 | p.S257P | missense | melanoma |
| FGFR2 | p.M536I | missense | endometrial cancer |
| FGFR2 | p.M536I | missense | endometrial cancer |
| FGFR2 | p.M536I | missense | endometrial cancer |
| FGFR2 | p.M538I | missense | endometrial cancer |
| FGFR2 | p.M538I | missense | endometrial cancer |
| FGFR2 | p.M538I | missense | endometrial cancer |
| FGFR2 | p.I548V | missense | endometrial cancer |
| FGFR2 | p.N550H | missense | endometrial cancer |
| FGFR2 | p.N550K | missense | endometrial cancer |
| FGFR2 | p.N550K | missense | endometrial cancer |
| FGFR2 | p.V565I | missense | endometrial cancer |
| FGFR2 | p.E566G | missense | endometrial cancer |
| FGFR2 | p.L618M | missense | endometrial cancer |
| FGFR2 | p.K660E | missense | endometrial cancer |
| FGFR2 | p.S252W | missense | endometrial cancer |
| FGFR2 | p.P253R | missense | cancer |
| FGFR2 | p.W290C | missense | lung squamous cell carcinoma |
| FGFR2 | p.S320C | missense | lung squamous cell carcinoma |
| JAK3 | p.Q501H | missense | megakaryocytic leukemia |
| JAK3 | p.Q501H | missense | megakaryocytic leukemia |
| JAK3 | p.R657Q | missense | megakaryocytic leukemia |
| JAK3 | p.I87T | missense | megakaryocytic leukemia |
| BRAF | p.E77* | nonsense | colorectal cancer |
| BRAF | p.LEQ76F* | nonsense | lung cancer |

SEQUENCE LISTING

```
<160> NUMBER OF SEQ ID NOS: 21

<210> SEQ ID NO 1
<211> LENGTH: 14
<212> TYPE: PRT
<213> ORGANISM: Homo sapiens
<220> FEATURE:
<221> NAME/KEY: Mutation
<222> LOCATION: (14)..(14)

<400> SEQUENCE: 1

Asp Leu Thr Val Lys Ile Gly Asp Phe Gly Leu Ala Thr Glu
1               5                   10

<210> SEQ ID NO 2
<211> LENGTH: 11
<212> TYPE: PRT
<213> ORGANISM: Homo sapiens
<220> FEATURE:
<221> NAME/KEY: Mutation
<222> LOCATION: (1)..(1)

<400> SEQUENCE: 2

Glu Lys Ser Arg Trp Ser Gly Ser His Gln Phe
1               5                   10

<210> SEQ ID NO 3
<211> LENGTH: 10
<212> TYPE: PRT
<213> ORGANISM: Homo sapiens
<220> FEATURE:
<221> NAME/KEY: Mutation
<222> LOCATION: (10)..(10)

<400> SEQUENCE: 3

Lys Ile Gly Asp Phe Gly Leu Ala Thr Glu
1               5                   10

<210> SEQ ID NO 4
<211> LENGTH: 12
<212> TYPE: PRT
<213> ORGANISM: Homo sapiens
<220> FEATURE:
<221> NAME/KEY: Mutation
<222> LOCATION: (12)..(12)

<400> SEQUENCE: 4

Met Thr Glu Tyr Lys Leu Val Val Val Gly Ala Asp
1               5                   10

<210> SEQ ID NO 5
<211> LENGTH: 18
<212> TYPE: PRT
```

```
<213> ORGANISM: Homo sapiens
<220> FEATURE:
<221> NAME/KEY: Mutation
<222> LOCATION: (1)..(1)

<400> SEQUENCE: 5

Asp Gly Val Gly Lys Ser Ala Leu Thr Ile Gln Leu Ile Gln Asn His
1               5                   10                  15
Phe Val

<210> SEQ ID NO 6
<211> LENGTH: 13
<212> TYPE: PRT
<213> ORGANISM: Homo sapiens
<220> FEATURE:
<221> NAME/KEY: Mutation
<222> LOCATION: (13)..(13)

<400> SEQUENCE: 6

Met Thr Glu Tyr Lys Leu Val Val Val Gly Ala Gly Asp
1               5                   10

<210> SEQ ID NO 7
<211> LENGTH: 17
<212> TYPE: PRT
<213> ORGANISM: Homo sapiens
<220> FEATURE:
<221> NAME/KEY: Mutation
<222> LOCATION: (1)..(1)

<400> SEQUENCE: 7

Asp Val Gly Lys Ser Ala Leu Thr Ile Gln Leu Ile Gln Asn His Phe
1               5                   10                  15
Val

<210> SEQ ID NO 8
<211> LENGTH: 17
<212> TYPE: PRT
<213> ORGANISM: Homo sapiens
<220> FEATURE:
<221> NAME/KEY: Mutation
<222> LOCATION: (17)..(17)

<400> SEQUENCE: 8

Asn Val Leu Val Lys Thr Pro Gln His Val Lys Ile Thr Asp Phe Gly
1               5                   10                  15
Arg

<210> SEQ ID NO 9
<211> LENGTH: 6
<212> TYPE: PRT
<213> ORGANISM: Homo sapiens
<220> FEATURE:
<221> NAME/KEY: Mutation
<222> LOCATION: (6)..(6)

<400> SEQUENCE: 9

Ile Thr Asp Phe Gly Arg
1               5

<210> SEQ ID NO 10
<211> LENGTH: 10
<212> TYPE: PRT
<213> ORGANISM: Homo sapiens
<220> FEATURE:
<221> NAME/KEY: Mutation
```

<222> LOCATION: (10)..(10)

<400> SEQUENCE: 10

Ala Ile Ser Thr Arg Asp Pro Leu Ser Lys
1               5                   10

<210> SEQ ID NO 11
<211> LENGTH: 6
<212> TYPE: PRT
<213> ORGANISM: Homo sapiens
<220> FEATURE:
<221> NAME/KEY: Mutation
<222> LOCATION: (1)..(1)

<400> SEQUENCE: 11

Lys Ile Thr Glu Gln Glu
1               5

<210> SEQ ID NO 12
<211> LENGTH: 13
<212> TYPE: PRT
<213> ORGANISM: Homo sapiens
<220> FEATURE:
<221> NAME/KEY: Mutation
<222> LOCATION: (13)..(13)

<400> SEQUENCE: 12

Ala Ile Ser Thr Arg Asp Pro Leu Ser Glu Ile Thr Lys
1               5                   10

<210> SEQ ID NO 13
<211> LENGTH: 8
<212> TYPE: PRT
<213> ORGANISM: Homo sapiens
<220> FEATURE:
<221> NAME/KEY: Mutation
<222> LOCATION: (8)..(8)

<400> SEQUENCE: 13

Asp Pro Leu Ser Glu Ile Thr Lys
1               5

<210> SEQ ID NO 14
<211> LENGTH: 25
<212> TYPE: PRT
<213> ORGANISM: Homo sapiens
<220> FEATURE:
<221> NAME/KEY: Mutation
<222> LOCATION: (25)..(25)

<400> SEQUENCE: 14

Lys Thr Leu Ser Ala Leu Asp Lys Thr Glu Gln Glu Ala Leu Glu Tyr
1               5                   10                  15

Phe Met Lys Gln Met Asn Asp Ala Arg
            20                  25

<210> SEQ ID NO 15
<211> LENGTH: 6
<212> TYPE: PRT
<213> ORGANISM: Homo sapiens
<220> FEATURE:
<221> NAME/KEY: Mutation
<222> LOCATION: (6)..(6)

<400> SEQUENCE: 15

Gln Met Asn Asp Ala Arg
1               5

```
<210> SEQ ID NO 16
<211> LENGTH: 7
<212> TYPE: PRT
<213> ORGANISM: Homo sapiens
<220> FEATURE:
<221> NAME/KEY: Mutation
<222> LOCATION: (7)..(7)

<400> SEQUENCE: 16

Met Pro Glu Ala Ala Pro Arg
1               5

<210> SEQ ID NO 17
<211> LENGTH: 22
<212> TYPE: PRT
<213> ORGANISM: Homo sapiens
<220> FEATURE:
<221> NAME/KEY: Mutation
<222> LOCATION: (1)..(1)

<400> SEQUENCE: 17

Val Ala Pro Ala Pro Ala Ala Pro Thr Pro Ala Ala Pro Ala Pro Ala
1               5                   10                  15

Pro Ser Trp Pro Leu Ser
            20

<210> SEQ ID NO 18
<211> LENGTH: 19
<212> TYPE: PRT
<213> ORGANISM: Homo sapiens
<220> FEATURE:
<221> NAME/KEY: Mutation
<222> LOCATION: (19)..(19)

<400> SEQUENCE: 18

Phe Thr Glu Asp Pro Gly Pro Asp Glu Ala Pro Arg Met Pro Glu Ala
1               5                   10                  15

Ala Pro Arg

<210> SEQ ID NO 19
<211> LENGTH: 22
<212> TYPE: PRT
<213> ORGANISM: Homo sapiens
<220> FEATURE:
<221> NAME/KEY: Mutation
<222> LOCATION: (22)..(22)

<400> SEQUENCE: 19

Glu Gln Trp Phe Thr Glu Asp Pro Gly Pro Asp Glu Ala Pro Arg Met
1               5                   10                  15

Pro Glu Ala Ala Pro Arg
            20

<210> SEQ ID NO 20
<211> LENGTH: 8
<212> TYPE: PRT
<213> ORGANISM: Homo sapiens
<220> FEATURE:
<221> NAME/KEY: Mutation
<222> LOCATION: (8)..(8)

<400> SEQUENCE: 20

Met Val Asp Val Gly Gly Pro Arg
1               5
```

```
<210> SEQ ID NO 21
<211> LENGTH: 10
<212> TYPE: PRT
<213> ORGANISM: Homo sapiens
<220> FEATURE:
<221> NAME/KEY: Mutation
<222> LOCATION: (1)..(1)

<400> SEQUENCE: 21

Arg Ser Glu Arg Arg Lys Trp Ile His Cys
1               5                   10
```

METHODS AND ANTIBODIES FOR DESIGNING AND DETECTING MUTATION-SPECIFIC OR HIDDEN EPITOPE/ANTIGENA

CROSS-REFERENCE TO RELATED APPLICATIONS

This application is a continuation-in-part of U.S. patent application Ser. No. 13/312,285, filed Dec. 6, 2011, which claims priority to Ser. No. 61/420,354 filed on Dec. 7, 2010.

TECHNICAL FIELD

The present description relates to methods, Artificially Cleaved Epitopes (ACEs), antibodies, reagents, immunoassays and kits for designing and detecting mutation site-specific epitopes or antigens, either in situ or ex situ in sample preparations, and their use thereof.

BACKGROUND OF THE INVENTION

A gene mutation is a permanent alteration in the DNA sequence that makes up a gene. Mutations can affect anywhere from a base pair to a large segment of a chromosome. Gene mutations can be classified in two major categories: (i) Germline or hereditary mutations are inherited from a parent and are present throughout a lifetime in virtually every cell in the body. Somatic or acquired mutations occur at some time periods during a lifetime and are present only in certain cells, not in every cell in the body. There are many different types of gene mutations, such as genetic code substitution, insertion, deletion or frameshift.

Cancers result from the accumulation of mutations in critical genes that alter normal programmes of cell proliferation, differentiation and death. Only about 5% to 10% of all cancers are thought to be related to germline mutations, and the rest are associated with somatic mutations. Fractions of neurodegenerative diseases such as Alzheimer disease (AD), Parkinson disease (PD), Huntington's disease (HD), and amyotrophic lateral sclerosis (ALS), are caused either by germline or somatic mutations (Kennedy et al., 2012).

Other common mutation-related disorders include, but not limited, 22q11.2 deletion syndrome, Angelman syndrome, Canavan disease, Charcot-Marie-Tooth disease, Color blindness, Cri du chat, Cystic fibrosis, Down syndrome, Duchenne muscular dystrophy, Haemochromatosis, Haemophilia, Klinefelter syndrome, Neurofibromatosis, Phenylketonuria, Polycystic kidney disease, Prader-Willi syndrome, Sickle-cell disease, Tay-Sachs disease, and Turner syndrome. The advances in molecular biology technologies have tremendously accelerated the discovery of causative genes. Despite this progress, however, the mutations causing a substantial number of diseases remain to be identified.

Mutations can occur at multiple sites of a same protein. For example, Factor XI mutation sites include: Met-18Ile, Ser-4Leu, Gly-1Arg, Asp16His, Val20Ala, Pro23Leu, Pro23Gln, Ser24Arg, Cys28Phe, Gln29His, Thr33Pro, Thr33Ile, Tyr35His, Cys38Arg, Cys38Trp, Pro48Leu, Pro52Leu, Arg54Pro, Thr57Ile, Cys58Arg, Cys58Phe, Cys58Tyr, Pro69Thr, Gly79Ala, Ser81Tyr, Lys83Arg, Gln88Stop, Cys92Gly, Met102Thr, Gly104Asp, Cys122Tyr, Thr123Met, Asp125Asp, His127Arg, Cys128Stop, Thr132Met, Tyr133Ser, Tyr133Cys, Ala134Pro, Arg144Cys, Gly155Glu, Leu172Pro, Ala181Val, Cys182Tyr, Arg184Gly, Pro188Ser, Asp198Asn, Cys212Ser, Cys212Arg, Phe221Ser, Ser225Phe, Glu226Arg, Trp228Cys, Arg234Lys, Arg234Ile, Arg234Ser, Cys237Tyr, Glu243Asp, Gly245Glu, Ser248Asn, Thr249Thr, Arg250Cys, Arg250His, Lys252Ile, Gly259Ser, Ile269Ile, Phe283Leu, Ile290Phe, Ile290Thr, Glu297Lys, Glu297Stop, Leu302Pro, Thr304Ile, Val307Phe, Arg308Cys, Cys309Stop, Thr313Ile, Cys321Phe, Glu323Lys, Gly336Arg, Ile341Met, Leu342Pro, Gly344Arg, Gly350Arg, Gly350Glu, Gly350Ala, Tyr351Ser, Tyr351Stop, Leu355Ser, Cys356Arg, Val371Ile, Gly372Ala, Ala375Val, Arg378Cys, Gly379Gly, Trp381Leu, Trp381Arg, Pro382Leu, Trp383Stop, Thr386Asn, His388Pro, Thr389Pro, Thr390Pro, Cys398Tyr, Gly400Ser, Gly400Val, Ser401Ala, Gln406Stop, Trp407Cys, Thr410Ile, Ala412Ser, Ala412Thr, Ala412Val, Arg425Cys, Cys427Tyr, Ser428Gly, Gln433Glu, Phe442Val, Glu447Stop, Gly460Arg, Thr475Ile, Arg479Stop, Cys482Arg, Cys482Trp, Ser485Pro, Tyr493His, Trp497Cys, Val498Met, Trp501Stop, Trp501Cys, Lys518Asn, Pro520Leu, Cys527Tyr, Gly544Ser, Glu547Lys, Asp551Asp, Gly555Glu, Asp556Gly, Cys563Phe Gene mutations may generate dysfunctional proteins, thus causing diseases. For example, the RAS-RAF-MEK-ERK-MAP kinase pathway regulates cellular growth. RAS mutation occurs in about 15% of human cancer. BRAF somatic missense mutations are found in 66% of malignant melanomas, among which a single substitution (V599E) accounts for 80%.

Gene mutations can be identified either by detecting mutated genes or the proteins encoded by mutated genes (referring to as mutant proteins hereafter). Some mutant proteins are disease-specific biomarkers, as identification of these mutant proteins is critical for disease diagnosis, staging, treatment, and prognosis. For that reason, mutation-specific antibodies are unmet needs for detecting mutation-related disease-specific biomarkers. In some cases, when a mutant protein is significantly different with the normal protein, an antibody may be generated to recognize specifically the mutant protein. However, a large number of disease-related mutant proteins are encoded by missense mutations, leading to only one amino acid substitutions in the mutant protein. For example, Wood et al. (2007) reported that the great majority of gene mutations are single-base substitutions (92.7%), with 81.9% resulting in missense changes. These subtle changes in mutant proteins make generating mutation-specific antibodies extremely difficult. For example, although v-Ki-ras2 Kirsten rat sarcoma viral oncogene homolog (KRAS) and tumor protein p53 (TP53) are two of the most commonly mutated and intensely studied cancer genes, there still are no antibodies that can reliably distinguish mutant from normal versions of these proteins (Wang et al., 2011). Therefore, novel method to generate mutation-specific antibodies is an unmet need for identifying mutant proteins.

SUMMARY OF THE INVENTION

The present invention discloses the "Artificially Cleaved Epitope" or ACE methods, antibodies, reagents, immunoassays and kits for designing and detecting mutation-specific epitopes/antigens, collectively defined as the ACE methods, and their use thereof.

The ACE methods encompass all or part of these steps: (a) Make an ACE antigen by designing, synthesizing or isolating the mutation-specific ACE structure; (b) Make ACE mutation-specific antibody with the mutation-specific ACE antigen by any antibody-making, antibody-like molecule-making methods, recombinant antibody making methods, single domain antibody making methods, and the like; (c) The mutation-specific ACE structure in sample preparations is not naturally or poorly accessible by antibody, and thus must be created artificially and precisely either in situ or ex situ by the designated hydrolytic enzyme or chemical agent treatment in a sequence- and amino acid dependent and residue chemical bond-specific manner; and (d) Detect mutation-specific ACE in situ or ex situ by any antibody-based method in any types of sample preparations. This invention also includes utilities and applications of the ACE methods, antibodies, reagents, immunoassays and kits.

In one embodiment, this invention provides unique mutation-specific ACE antigen design methods, wherein the ACE structure must possess one or combinations of these characters: (a) must be antigenic, (b) must be a complete or truncated form of an artificially chemical bond-specific hydrolytic enzyme- or agent-cleaved segment (i.e., ACE); (c) must be artificially and specifically created and/or exposed in a sequence-dependent and residue chemical bond-specific manner in samples or sample preparations (e.g., in Western blot membranes, tissues or cell lysates, tissue sections, isolated or culture cells, isolated fractions, any ACE-containing surfaces/matrices/materials, and the likes); and (d) the hidden or mutation-specific epitopes may be amino acids/peptides, sugar monomers/polymers, lipids/ lipid linkers (e.g., ethanolamine), nucleic acids, ADP-ribose, or their combinations. A basic mutation-specific epitope/ antigen ACE structure is "$H_2N$-A3-A2-A1-Am(s)-A1'-A2'-A3'-COOH", and a basic non-mutation-specific epitope/ antigen ACE structure "$H_2N$-A3-A2-A1-An(s)-A1'-A2'-A3'-COOH", wherein A1, A2, A3, Am(s) or An(s), A1', A2' A3' are amino acid residue(s) of a polypeptide/protein, wherein $H_2N$-indicates the N-terminal direction and —COOH implies the C-terminal direction, wherein Am(s) is the mutated amino acid residue(s) that is different with the corresponding non-mutated amino acid residue(s) of An(s) in the non-mutation polypeptide/protein, wherein the covalent chemical bond(s) between Am(s) and its adjacent amino acid residues at either the N-terminal or C-terminal direction can be artificially, specifically and precisely cleaved by designed chemical bond-specific hydrolysis in samples and sample preparations to create (the new terminals) and/or expose said mutation-specific ACE structure for designing epitopes, making antibodies and mutation-specific epitopes/ antigens detection.

In another embodiment, the invention provides methods of using ACE antigen to make antibodies including, but not limited to, polyclonal, monoclonal, bi-specific, recombinant, humanized, antibody-like molecules, and the likes.

In a further embodiment, the invention provides methods of detecting ACE structures in samples and sample preparations, wherein ACE in a sample is poorly accessible or unrecognizable by antibodies, and thus must be artificially created (with new terminals) and/or exposed specifically and precisely, rather than randomly or accidentally, by residue chemical bond-specific hydrolytic enzymes or agents; wherein said hydrolytic enzymes and agents are specifically selected and should be mostly the same, but may also be different, with the one(s) used for the hydrolysis-guided ACE antigen design; wherein artificially, specifically and precisely creating (new terminals) and/or exposing hidden ACE antigens can be carried out in any samples or sample preparations including, but not limited to, in vivo or in vitro, in whole or part of biological bodies or organisms, in isolated organs or organelles, in tissues or tissue sections (with or without fixation), in isolated or cultured cells, in tissue or cell lysates, in body fluids or cell culture medium, as well as in biochemical assay mixtures, on Western blot or chromatographic membranes or any supporting matrices or surfaces, in chromatographic and centrifuge fractions, in cellular or subcellular fractions, and the likes.

In an additional embodiment, the inventive ACE methods can be used to reduce non-specific bindings in all antibody-based applications. This utility is owing to the fact that the chemical bond-specific hydrolysis is able to specifically and precisely create and/or expose the ACE structures, while breaking up other structures/epitopes that are otherwise able to bind to the ACE antibody non-specifically.

The inventive ACE methods, antibodies, reagents, immunoassays and kits can be used in all antibody-based applications, including, but not limited to, Western blot, immunocytochemistry, immunofluorescence, immunoelectron microscopy, immunoprecipitation, flow cytometry, Enzyme-Linked Immuno-Sorbent Assay (ELISA), peptide array, antibody array, or any other types of immunoassays, and the like.

The inventive ACE methods, antibodies, reagents, immunoassays and kits can be employed in a number of areas, including, but not limited to: (a) determination of mutation-specific epitopes or sequences, (b) monitoring changes in mutation sites in vivo and in vitro, (c) diagnosis of diseases, (d) development of therapeutic agents for treatment of diseases, and (g) the likes.

A few examples of diagnosing diseases with the ACE methods, antibodies, reagents, immunoassays, and kits may include, but are not limited to: (a) somatic or germline mutation-related diseases; (b) cancer; (c) neurological, neurodegenerative; and (c) inherited diseases; (d) mutation-related biomarkers, and (e) the like.

The ACE methods, antibodies and reagents can be used in therapeutic applications including, but not limited to, those related to gene mutations.

The ACE methods, antibodies, reagents, and immunoassays can be assembled to kits for research, diagnostic and therapeutic applications.

BRIEF DESCRIPTION OF THE DRAWINGS

All hidden antigens designed below are derived from the mutation-specific epitope/antigen ACE basic structure "$H_2N$-A3-A2-A1-Am(s)-A1'-A2'-A3'-COOH", and the non-mutation-specific epitope/antigen ACE basic structure "$H_2N$-A3-A2-A1-An(s)-A1'-A2'-A3'-COOH", as described above in the section (SUMMARY OF THE INVENTION). In exemplary ACE structures described in this invention, the single capital letters represent one-letter standard amino acid abbreviations. KLH all together is the abbreviation for Keyhole Limpet Hemocyanin, which is one of the most commonly used immunogenic carriers for antibody production. The dash "-" represents covalent chemical bond conjugation.

FIG. 1. Schematic drawings of the ACE structures. $H_2N$ represents the N-terminal direction, and COOH indicates the C-terminal direction from the Am(s) or An(s) residue(s). A1, A2, A3, Am(s), An(s), A1', A2', A3' are amino acid residue(s) of a mutant or non-mutant polypeptide/protein, Am(s) is the mutated amino acid residue(s). An(s) is the corresponding normal or non-mutation amino acid residue(s). The covalent chemical bond(s) between Am(s) or An(s) and its adjacent amino acid residues at either the N-terminal or C-terminal direction can be artificially, specifically and precisely cleaved by designed chemical bond-specific hydrolysis in samples and sample preparations to create (the new terminals) and/or expose said mutation-specific or hidden ACE structure or non-mutation-specific ACE structure for designing mutation-specific epitope, making mutation-specific antibodies and for mutation-specific epitope/antigen detection.

FIG. 1A The mutation-specific epitope/antigen ACE structure "$H_2N$-A3-A2-A1-Am(s)-A1'-A2'-A3'-COOH".

FIG. 1B, Non-mutation-specific epitope/antigen ACE structure "$H_2N$-A3-A2-A1-An(s)-A1'-A2'-A3'-COOH".

FIG. 2. The following are exemplary designs of BRAF mutation-specific ACE epitopes/antigens. SEQ ID NOS 1-3 are assigned to these sequences in FIG. 2 throughout this application. BRAF is a human gene that makes a protein called B-raf that is a serine/threonine kinase. Approximately 90% of known BRAF mutations are V600E mutations which are found in many types of cancers such as sarcoma, metastatic melanoma, ovarian serous carcinoma, and pilocytic astrocytoma. This mutation leads to elevated kinase activity for inducing cell transformation. V600E mutation-specific epitopes/antigens are designed as: (i) DLTVKIGDFGLATE$_{600}$ (SEQ ID NO 1) when Glutamyl endopeptidase or Staphylococcal peptidase I is used as the hydrolytic enzyme, wherein subscription 600 indicates the glutamate (E) at residue 600 of human B-raf protein; (ii) E$_{600}$KSRWSGSHQF (SEQ ID NO 2), when Asp-N endopeptidase+N-terminal Glu are used as the hydrolytic enzymes; and (iii) KIGDFGLATE$_{600}$ (SEQ ID NO 3) when LysN Peptidyl-Lys metalloendopeptidase is used as the hydrolytic enzyme.

FIG. 3. The following are exemplary designs of Kirsten ras (KRAS) mutation-specific ACE epitopes/antigens. KRAS oncogene is a human gene that makes a protein called K-ras. K-ras mutations occur in over 90% of pancreatic carcinomas. The ras pathway rallies growth-promoting signals affecting the production and regulation of other key proteins. Mutation analysis of the KRAS oncogene is now established as a predictive biomarker in colorectal cancer (CRC). The most frequent types of mutations are glycine to aspartate on codon 12 (G12D, 36.0%), and glycine to aspartate on codon 13 (G13D, 18.8%). They account for 76.6% of all mutations and prevail in primary tumors and distant metastases (Neumann et al., 2009). SEQ ID NOS 4-7 are assigned to these sequences in FIG. 3 throughout this application.

FIG. 3A. K-ras mutation-specific epitopes/antigens are designed as: (i) MTEYKLVVVGAD$_{12}$ (SEQ ID NO 4), when formic acid is used as the hydrolytic agent, wherein subscription 12 indicates the aspartate (D) at residue 12 of the K-ras protein; and (ii) D$_{12}$GVGKSALTIQLIQNHFV (SEQ ID NO 5) when Asp-N endopeptidase is used as the hydrolytic enzyme.

FIG. 3B. K-ras mutation-specific epitope/antigens are designed as: (i) MTEYKLVVVGAGD$_{13}$ (SEQ ID NO 6), when formic acid is used as the hydrolytic agent; and (ii) D$_{13}$VGKSALTIQLIQNHFV (SEQ ID NO 7), when Asp-N endopeptidase is used as the hydrolytic enzyme.

FIG. 4. The following are exemplary designs of epidermal growth factor receptor (EGFR) mutation-specific ACE epitopes/antigens. Approximately 10% of patients with non small cell lung cancer (NSCLC) in the US and 35% in East Asia have tumor associated EGFR mutations. About 90% of these mutations are exon 19 deletions or exon 21 L858R point mutations. These mutations increase the kinase activity of EGFR, leading to uncontrolled cell growth. SEQ ID NOS 8-9 are assigned to these sequences in FIG. 4 throughout this application. EGFR mutation-specific epitope/antigens are designed as: (i) NVLVKTPQHVKITDFGR$_{858}$ (SEQ ID NO 8) when Arg-C proteinase or Clostripain is used as the hydrolytic enzyme or agent, wherein subscription 858 indicates the arginine (R) at residue 858 of the EGFR protein; and (ii) ITDFGR$_{858}$ (SEQ ID NO 9), when trypsin or Thermolysin is used as the hydrolytic enzyme.

FIG. 5. The following are exemplary designs of phosphatidylinositol-4,5-bisphosphate 3-kinase, catalytic subunit alpha (PIK3CA) E542K, E545K, and H1047R mutation-specific epitopes/antigens. PIK3CA E542K, E545K, or H1047R mutation results in an amino acid substitution at position 542, 545, or 1047, respectively, in PIK3CA, from a glutamic acid (E) to a lysine (K) or a histidine to an arginine (R). These mutations increase the catalytic activity and thus may result in oncogenic transformation. SEQ ID NOS 10-15 are assigned to these sequences in FIG. 5 throughout this application.

FIG. 5A. PIK3CA E542K mutation-specific epitopes/antigens are designed as: (i) AISTRDPLSK$_{542}$ (SEQ ID NO 10) when LysC Lysyl endopeptidase (*Achromobacter* proteinase I) is used as the hydrolytic enzyme, wherein subscription 542 indicates the lysine (K) at residue 542 of the PIK3CA protein; and (ii) K$_{542}$ITEQE (SEQ ID NO 11), when LysN Peptidyl-Lys metalloendopeptidase is used as the hydrolytic enzyme.

FIG. 5B. PIK3CA E545K mutation-specific epitopes/antigens are designed as: (i) AISTRDPLSEITK$_{545}$ (SEQ ID NO 12) when LysC Lysyl endopeptidase (*Achromobacter* proteinase I) is used as the hydrolytic enzyme; and (ii) DPLSEITK$_{545}$ (SEQ ID NO 13) when trypsin is as the hydrolytic enzyme.

FIG. 5C PIK3CA H1047R mutation-specific epitopes/antigens are designed as: (i) KLDKTEQEALEYFMKQMNDTLAAR$_{1047}$ (SEQ ID NO 14) when Arg-C proteinase or Clostripain is used as the hydrolytic enzyme or agent; and (ii) QMNDAR$_{1047}$ (SEQ ID NO 15) when trypsin is used as the hydrolytic enzyme.

FIG. 6. Tumor Protein P53 (TP53) acts as a tumor suppressor in many tumor types. TP53 somatic mutations are one of the most frequent alterations in human cancers and thus potential prognostic and predictive markers, as well as targets for pharmacological intervention. Most mutations are single-base substitutions distributed throughout the coding sequence. All TP53 mutations currently known can be found in the Database (http://www-p53.iarc.fr/). P72R is a mostly studied TP53 mutation (Olivier et al., 2010). SEQ ID NOS 16-19 are assigned to these sequences in FIG. 6 throughout this application.

FIG. 6A. TP53 P72R mutation-specific epitopes/antigens can be designed as: (i) MPEAAPR$_{72}$ (SEQ ID NO 16) or V$_{73}$APAPAAPTPAAPAPAPSWPLS (SEQ ID NO 17) when Arg-C proteinase or Clostripain is used as the hydrolytic enzyme or agent, wherein subscription 72 indicates the 72 arginine (R) or 73 valine (V) residue of human TP53 protein FIG. 6B. TP53 P72R mutation-specific epitopes/antigens can also be designed as: (i) FTEDPGPDEAPRMPEAAPR$_{72}$ (SEQ ID NO 18), when Thermolysin is used as the hydrolytic enzyme; and (ii) EQWFTEDPGPDEAPRMPEAAPR$_{72}$ (SEQ ID NO 19) when Thrombin is used as the hydrolytic enzyme.

FIG. 7. A-K: Examples of human genes, gene-encoded protein mutation sites, mutation types, and mutation-related diseases. Gene=gene name. Mutation site=mutated amino acid residue. For instance, GNA11 p.Q209P represents that the amino acid residue 209 glutamine (Q) is mutated by substitution with a proline (P). The non-mutated protein sequences can be found from the website: http://www.uniprot.org/. For example, the sequence of the first gene GNA11 non-mutated amino acid residues 191-220 is "-EYPFDLENIIFRMVDVGGQ$_{209}$RSERRKWIHCF-", wherein the residue 209 Q is replaced with a P in the mutant protein. Therefore, the sequence of the mutant protein amino acid residue 191-220 is "-EYPFDLENIIFRMVDVGGP$_{209}$RSERRKWIHCF-", wherein a GNA11 p.Q209P mutation site-specific epitope/antigen can be designed as: MVDVGGPR (SEQ ID NO 20) when Arg-C proteinase, Clostripain or Trypsin is used as the hydrolytic enzyme or agent. Another example is the GNA11 p.Q209L mutation which has a mutant sequence: "-EYPFDLENIIFRMVDVGGL$_{209}$RSERRKWIHCF-", wherein a GNA11 p.Q209P mutation site-specific epitope/antigen can be designed as: RSERRKWIHC (SEQ ID NO 21) when pepsin is used as the hydrolytic enzyme or agent.

FIG. 7A. A list of the gene name, the gene-encoded protein mutation sites, the mutation types, and the mutation-related diseases.

FIG. 7B. Continuation of the list FIG. 7A
FIG. 7C. A Continuation of the list FIG. 7B.
FIG. 7D. Continuation of the list FIG. 7C.
FIG. 7E. Continuation of the list FIG. 7D.
FIG. 7F. Continuation of the list FIG. 7E.
FIG. 7G. Continuation of the list FIG. 7F.
FIG. 7H. Continuation of the list FIG. 7G.
FIG. 7I. Continuation of the list FIG. 7H.
FIG. 7J. Continuation of the list FIG. 7I.
FIG. 7K. Continuation of the list FIG. 7J.

DETAILED DESCRIPTION

The invention summarized above may be better understood by referring to the following description, which should be read in conjunction with the accompanying claims and drawings in which like reference numbers are used for like parts. This description in which some examples of the embodiments of the inventions are shown, is to enable one to build and use an implementation of the invention, and is not intended to limit the invention, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent methods, designs, constructs, antibodies, kits, samples, and cell lines do not depart from the spirit and scope of the invention in its broadest form.

Definitions:

As used herein, the term "detection" or "detecting" is interchangeable with discovering, uncovering, finding, recognizing, revealing, determining, examining, measuring, and the like.

As used herein, "in situ" refers to a phenomenon or event occurred in exactly the original location, both in vivo and in vitro, including but not limited to, in whole or part of biological bodies or organisms, in isolated organs, cells, and organelles, in tissues or tissue sections (with or without fixation), in isolated or cultured cells, in body fluids or cell culture media, as well as on Western blot membranes, and any supporting matrices or surfaces, in chromatographic and centrifuge fractions, in reaction mixtures, and the like.

As used herein, "ex situ" is the opposite of "in situ", and refers to a phenomenon or event that does not occur in the original place both in vivo and in vitro.

As used herein, the term "hidden antigen" is often interchangeable with "hidden hapten or segment" or "ACE structure", and refers to an antigen epitope/segment/structure that, in its intact or natural form, is less antigenic and/or poorly accessible to large molecules including, but not limited to, antibodies. For example, an ACE structure may be a mutation site(s), macromolecule-to-macromolecule conjugation site, or a segment normally located inside its parent macromolecule, or may be covered by other surrounding molecules/structure(s)/cell membranes either in situ or ex situ, and thus is poorly or not accessible to antibodies.

As used herein, the term "macromolecule" refers to a polymeric molecule with more than 2 same or different units, either in a linear or branched sequence, including, but not limited to, polypeptides, polysaccharides, lipids or phospholipids, and nucleic acids, poly(ADP-ribose), or any combinations of the above.

As used herein, the term "carbohydrate" is interchangeable with the term "saccharide", typically referring to either polymeric or monomeric sugar molecules.

As used herein, the term "mutation site-specific hapten" refers to a segment that contains a macromolecular mutation site, which may need to be linked to an immunogenic carrier in order to become a complete antigen.

As used herein, the term "mutation site-specific antibody" refers to antibody that can specifically recognize a mutation site.

As used herein, the term "sidechain" refers to a chemical group that is attached to or branches from a core part of the molecule called the "mainchain" or backbone. In polymers, side chains extend from a backbone structure.

As used herein, the term "hydrolytic enzyme" refers to proteases, glycosidases, lipases or phospholipases, nucleases, and the like, which are currently known or will be identified in the future and are capable of cleaving particular chemical bonds in macromolecules in a site-specific manner.

As used herein, the term "agent", may be interchangeable with "hydrolytic agent" or "chemical agent", and refers to chemicals or any other non-biological materials that are currently known or will be identified in the future, and are capable of cleaving particular chemical bonds in macromolecular backbones in a site-specific manner. Hydrolytic agents may include, but are not limited to, 2-nitro-5-thiocyanobenzoic acid (NTCB)+Ni that cleaves the peptide bond at cysteine loci (Degani and Patchornik, 1974); cyanogen bromide (CNBr) that cleaves at methionine loci; BNPS-skatole [2-(2-nitrophenylsulfenyl)-3-methylindole] that cleaves at tryptophan loci; and formic acid that cleaves at aspartate loci in protein backbones.

Hydrolytic proteases and agents include, but are not limited to, Arg-C proteinase, Asp-N endopeptidase, Asp-N endopeptidase+N-terminal Glu, BNPS-Skatole, caspase1, caspase2, caspase3, caspase4, caspase5, caspase6, caspase7, caspase8, caspase9, caspase10, chymotrypsin, clostripain (clostridiopeptidase B), CNBr, enterokinase, factor Xa, formic acid, glutamyl endopeptidase, granzymeB, hydroxylamine, iodosobenzoic acid, LysC, LysN, NTCB (2-nitro-5-thiocyanobenzoic acid), pepsin, proline-endopeptidase, proteinase K, staphylococcal peptidase I, tobacco etch virus protease, thermolysin, thrombin, trypsin, and the like.

The chemical bond-cleaving site specificities of hydrolytic enzymes or agents can be found in publicly accessible databases including, but not limited, to Swiss-Prot ExPASy and the National Center for Biotechnology Information.

Glycosidases include, but are not limited to, exoglycosylase, endoglycosylase, any combination of exoglycosylase and endoglycosylase, and/or sialidase, fucosidase, mannosidase, galactosidase, xylosidase, and the like.

Lipases include, but are not limited to, triglyceride lipase, pancreatic lipase, lysosomal lipase, hepatic lipase, hormone-sensitive lipase, endothelial lipase, lingual lipase, and the like.

Phospholipases include, but are not limited to, phospholipase A1, phospholipase A2, phospholipase B, phospholipase C, phospholipase D, GPI-phospholipase C, GPI-phospholipase D, and the like.

Enzymes used in the invention may be natural, recombinant or chemically synthesized. They may be substantially pure, partially purified, or present in a crude biological sample.

As used herein, the term "organism" refers to all cellular life-forms including, but not limited to, prokaryotes and eukaryotes, non-cellular life-forms, and nucleic acid-containing entities including, but not limited to, bacteriophages and viruses.

As used herein, the term "sample or sample preparation" refers to a collection of inorganic, organic or biochemical molecules either in a pure or mixture form, either in nature (e.g., in a biological- or other specimen) or artificial type, either in heterogeneous or homogeneous form, either in isolated, partially isolated or non-isolated form, or either in solution or in a form immobilized or semi-immobilized on any supporting materials including but not limited to electrophoresis matrix (e.g., gel or capillary), Western blot membrane (e.g., nitrocellulose membranes), agarose support (e.g., gel or bead), nano particles, any supporting surface, cell culture plates, multiplex beads, or chromatographic supporting matrix, sucrose gradient medium. "Sample" further refers to a biological sample.

As used herein, the term "organism" refers to all cellular life-forms, including but not limited to prokaryotes and eukaryotes, as well as non-cellular life-forms, nucleic acid-containing entities, including but not limited to bacteriophage and viruses.

As used herein, the terms "biological sample" refer to a collection of a whole organism or a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen). "Biological sample" further refers to a homogenate, lysate, subcellular fraction or extract prepared from a whole organism or a subset of its tissues, cells or component parts, or a portion thereof. "Biological sample" also refers to sample preparations including but not limited to on electrophoretic and chromatographic gels, on Western, Southern, and Northern blot membranes, in isolated organelles, and in separated fractions.

As used herein, the term "tissue section" refers to a thin slice prepared from a whole organism or a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen).

As used herein, the term "mutation site-specific antibody" further refers to one or more antibodies, and also referred to as immunoglobulins. Mutation site-specific antibody may be natural or partially or wholly produced artificially, e.g. recombinant, or antibody fragments. A mutation site-specific antibody may be monoclonal or polyclonal, humanized, VHHs bispecific, and heteroconjugate antibodies, as well as antibody-like binding partners (e.g., phage display antibody-like fusion protein). Mutation site-specific antibody may be made in all immunoreactive animals or organisms including but not limited to rabbit, rat, camelids, mouse, sheep, horse and donkey. The antibody may, in some cases, be a member of one, or a combination immunoglobulin classes, including: VHHs, IgG, IgM, IgA, IgD, and IgE, as well as antibody-like molecules.

As used herein, the term "non-mutation site-specific antibody" refers to one or more antibodies that recognize the normal amino acid residues corresponding to the mutation site in the normal protein rather than the corresponding mutated residues in the mutant protein.

As used herein, the term "pan antibody" refers to one or more antibodies that recognize epitopes that are not located on the mutation site.

The mutation site-specific haptens or antigens may be used to select its binding partners by, for example, phage display or yeast display. The haptens or antigens include, but are not limited to, any chemical monomers or polymers, amino acids or peptides, carbohydrates, lipids or phospholipids, nucleotides, poly (ADP-riboses), and the like.

As used herein, the term "antigenicity' refers to the antigen capacity to stimulate the production of antibodies and the capacity to react with antibodies.

As used herein, the term "primary antibody" refers to antibody raised against an epitope of interest. The epitope can be a protein, peptide, carbohydrate, lipid, phospholipid, nucleic acid, any combination of the above, or any other macromolecules.

As used herein, the term "secondary antibody" refers to an antibody that binds to primary antibodies or antibody fragments. They are typically labeled with measurable probes for detection, purification, or cell sorting applications.

As used herein, the term "immunoassay" refers to any antibody-based measurement of the content of any substance in a sample. The presence of antigen and/or antibody can be assayed. The most common method is to label either antigen or antibody with any suitably detectable materials including, but not limited to, enzymes, radioisotopes, magnetic or fluorescent labels, or nanoparticles.

As used herein, the term "Western blot" or its interchangeable term "immunoblot" refers to an analytical method for detection of proteins or modified proteins in a sample. It uses gel electrophoresis to separate molecules in a sample. The separated molecules are then transferred to a membrane (typically nitrocellulose) that can hold the macromolecules, where such macromolecules of interest can be detected specifically with antibodies.

As used herein, the term "Enzyme-Linked ImmunoSorbent Assay" or "ELISA" refers to any method of detecting the presence and level of an antibody or an antigen in a sample. There are several variants of ELISA, including, but not limited to, sandwich ELISA, competitive ELISA, indirect ELISA, ELISA Reverse and the like. The most common procedure is to coat an antibody or antigen onto a surface, and then to add molecules of interest (antigen or antibody) to the precoated surface so that an antibody to antigen complex can form. The tagged antibodies or antigens, or the added secondary antibody with a detectable tag, can then be detected with a readout system.

As used herein, the term "immunohistochemistry" commonly refers to a method of antibody-based localization of antigens in a sample, commonly in a tissue section. An antibody to antigen interaction can be visualized by microscopy at the cellular level via any detectable means including, but not limited to, antibodies tagged by fluorophors, chromospheres or luminescence, or any detectable tags with any combinations of the above, including, but not limited to, peroxidase and its variants, chemiluminescence and its variants, and fluorescent molecules such as fluorescein isothiocyanate (FITC), Texas Red, rhodamine (TRITC), coumarin, cyanine, Alexa Fluors and the DyLight Fluors, and their derivatives.

As used herein, the term "immunocytochemistry" is often interchangeable with immunohistochemistry. Immunocytochemistry emphasizes a method of using antibodies to detect specific antigens at the cellular level. Immunocytochemistry may differ somewhat from immunohistochemistry in that it is often performed on samples of intact cells, whereas immunohistochemical samples are usually on tissue sections.

As used herein, the term "immunoprecipation" refers to a technique of antibody precipitating its antigen molecule out of mixture samples. This process is often used to isolate and concentrate a particular antigen or antigen complex from other molecules in a sample. Immunoprecipitation often requires coupling antibody-antigen complexes to a solid support substance in the procedure for separation of antibody-antigen complexes from other molecules in a sample.

As used herein, the term "co-immunoprecipitation" refers to immunoprecipitation of intact antigen complexes.

As used herein, the term "flow cytometry" refers to a method of counting, examining, and sorting particles suspended in a stream of fluid. It allows simultaneous multi-parametric analysis of the physical and/or chemical characteristics of single cellular particles flowing through an optical and/or electronic detection apparatus.

As used herein, "artificially cleaved epitope or ACE" refers to an epitope that is artificially cleaved for creating more antigenic and accessible epitope to antibody for detection or forming antibody-to-ACE complex purpose.

The "Artificially Cleaved Epitope" or "ACE" does not include naturally cleaved antigens in vivo.

As used herein, "hydrolysis-guided ACE design or ACE design" refers to antigen design methods that use an artificially cleaved epitope (ACE) as a hapten or antigen. The ACE is not naturally accessible to antibody or antibody-like molecules but can be artificially, specifically and precisely created and/or exposed in a sample by the chemical bond-specific hydrolysis of macromolecules.

As used herein, "hydrolysis-guided ACE antibody production" is interchangeable with "ACE antibody production" refers to making antibody with an ACE hapten or antigen designed by the ACE design methods.

As used herein, "residue" and "monomer" (of macromolecules) is often interchangeable, refers to a specific unit within polymeric chains of peptides, polysaccharides, lipids, nucleic acids, poly(ADP-ribose), and the like.

As used herein, "create or expose" (of ACE antigen) is often interchangeable.

As used herein, the term "create" refers to artificially creating ACE structures with free terminals in samples or sample preparations for antibody detection.

As used herein, "ACE methods" refers to a group of collective techniques including, but not limited to: (i) ACE design, (ii) making ACE antibody, (iii) ACE exposure and detection either in situ or ex situ in a sample, and (iv) ACE method applications. The ACE methods require to use: (a) structural and sequence information of molecular conjugates or linear hidden antigen, (b) chemical bond-cleaving specificities and properties of hydrolytic enzymes and agents, and (c) ACE exposure and detection methods.

1. Methods of Design Ace Antigens

This invention provides the novel "hydrolysis-guided ACE methods" or simply "ACE methods", including, but not limited to, all or part of these steps: (i) selecting a specific hydrolytic enzyme or chemical agent-cleaved mutation site-specific or a hidden ACE sequence or its truncated form; (ii) the ACE structure is a non-cleaved segment of an intact macromolecule in vivo, and is either poorly antigenic, or inaccessible by antibody, but can be artificially, specifically and precisely created and/or exposed by the residue chemical bond-specific hydrolytic enzyme, agent or their combinations, (iii) conjugate the ACE hapten to an immunogenic carrier for making it a complete antigen, (iv) a spacer including but not limited to GGG (glycine-glycine-glycine) may sometimes be added to increase the flexibility of the ACE, (v) use the complete antigen to make the antibodies or antibody-like molecules or binding partners, (vi) remove non-specific antibodies to the mutation site by negative absorption with the non-mutation peptide(s), (vii) create and/or expose the ACE artificially, specifically and precisely, rather than randomly or accidentally, either in situ or ex situ in any sample preparations by the specifically designated chemical bond-specific hydrolytic enzyme or means, and (viii) detect or image the ACE structure in sample preparations by antibody-based methods.

Figure 1B:
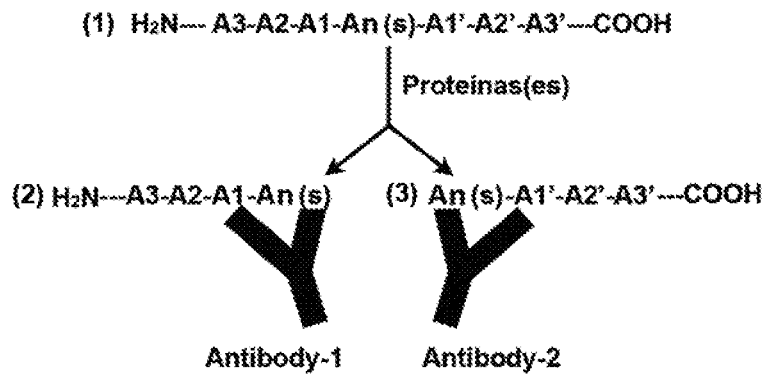
Figure 2:
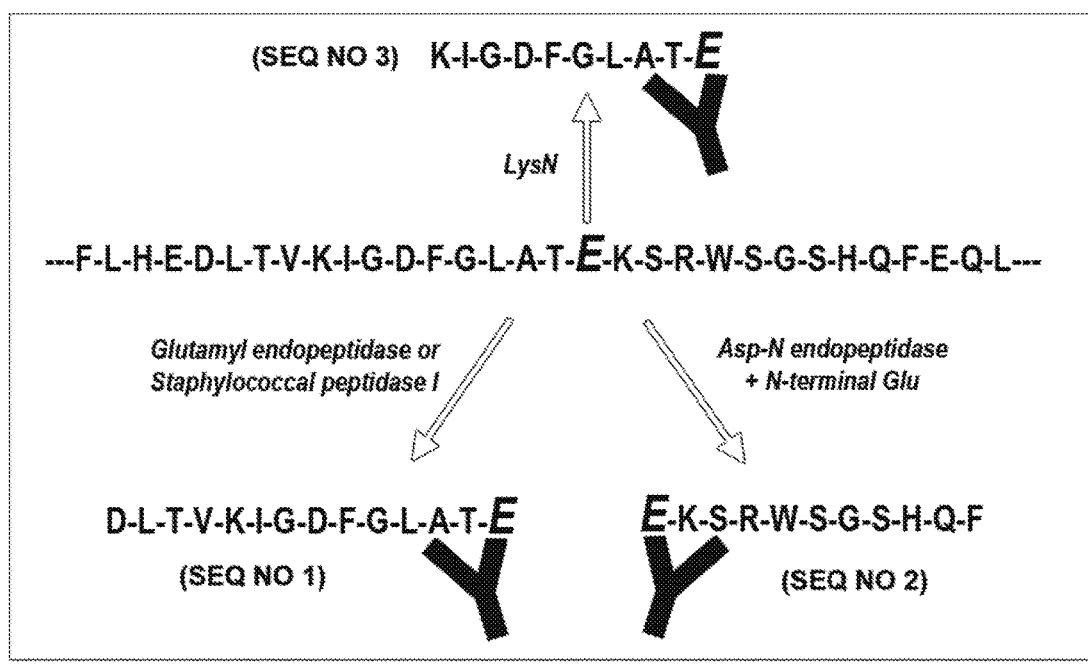
Figure 3A:
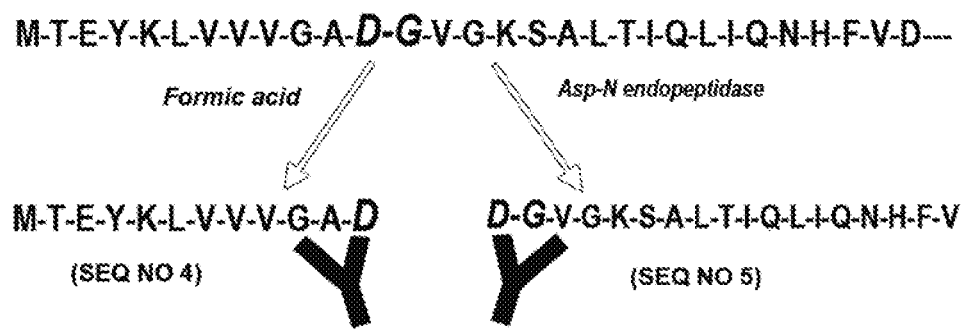
Figure 3B:
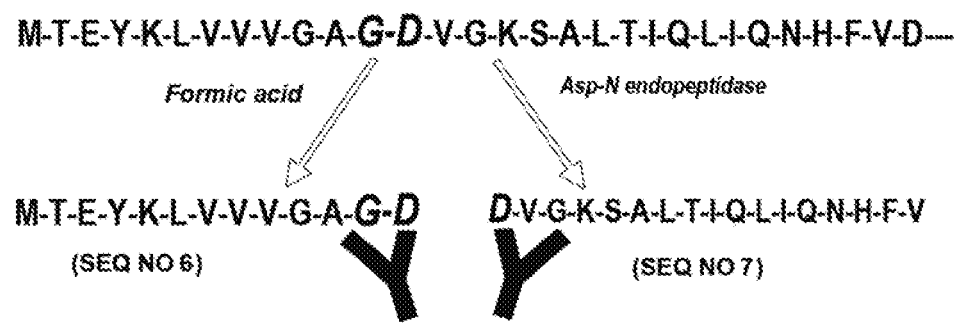
Figure 4:
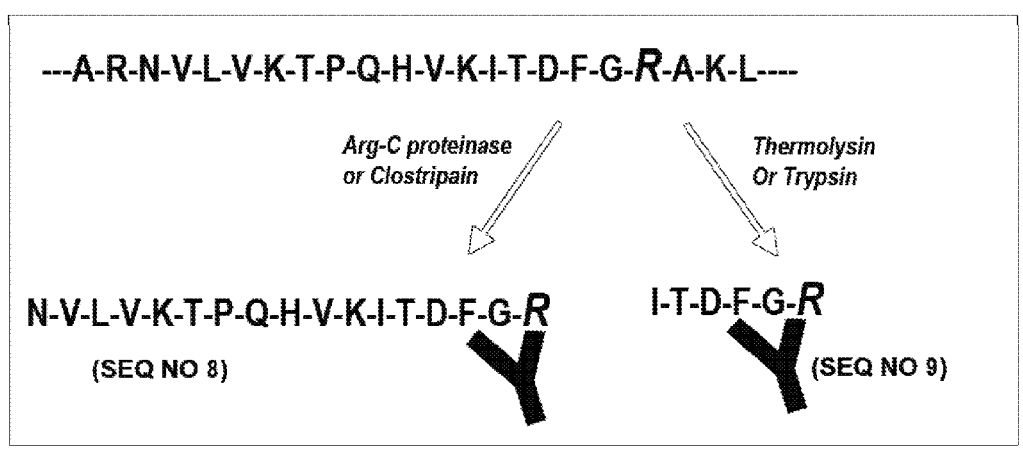
Figure 5A:
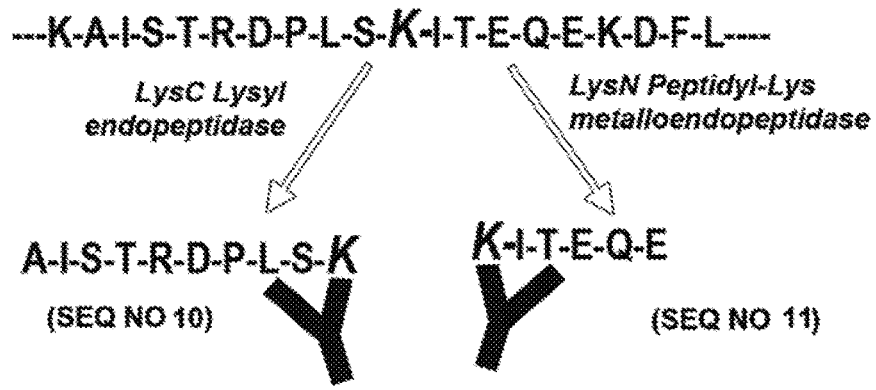
Figure 5B:
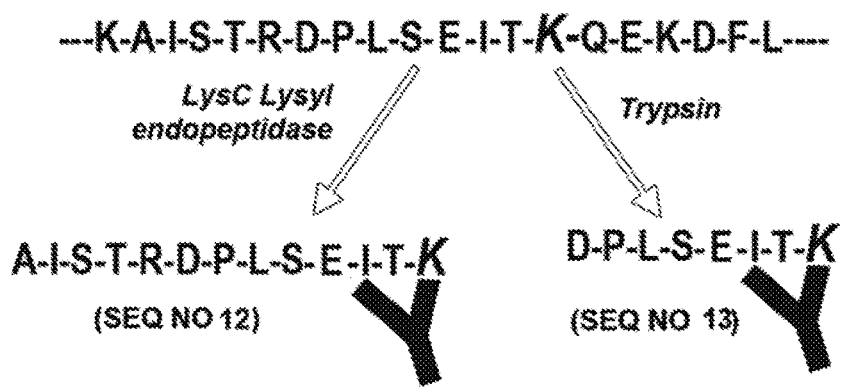
Figure 5C:
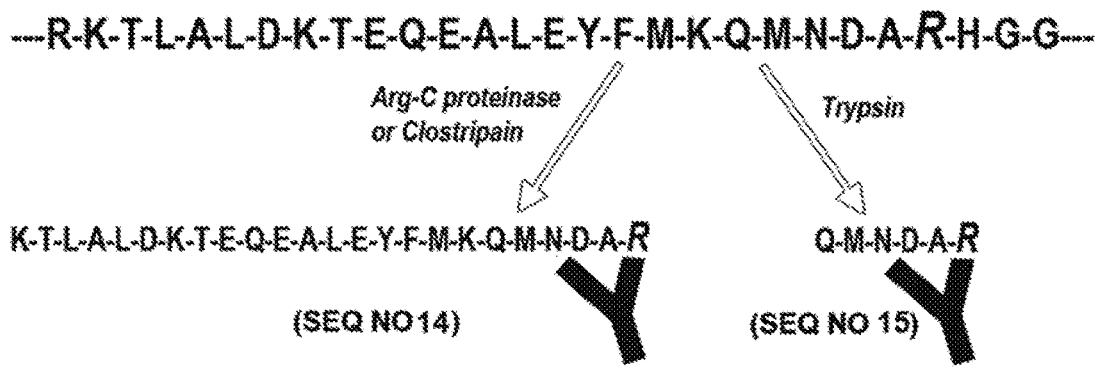
Figure 6A:
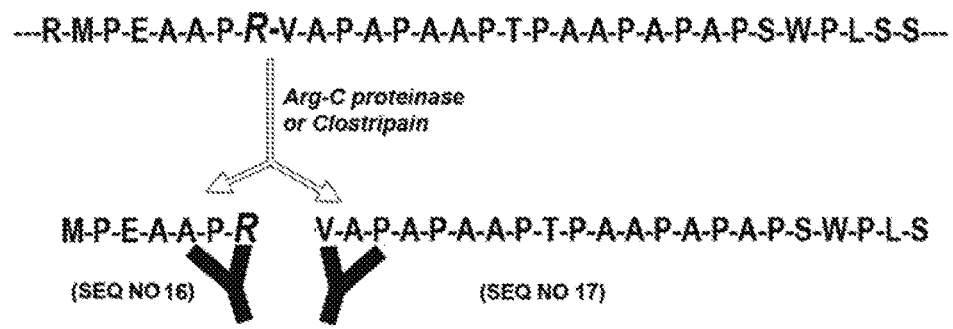
Figure 6B:
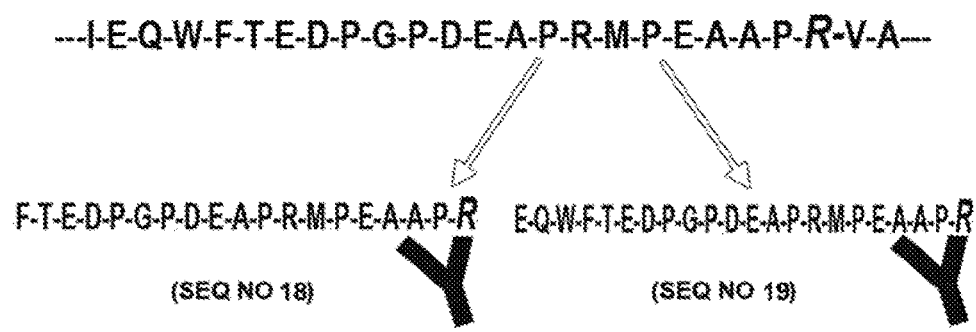

The mutation-specific ACE has a basic structure is $H_2N$-A3-A2-A1-Am(s)-A1'-A2'-A3'-COOH, and the corresponding non-mutation specific epitope/antigen ACE structure is $H_2N$-A3-A2-A1-An(s)-A1'-A2'-A3'COOH, wherein $H_2N$-A3-A2-A1-Am(s)-A1'-A2'-A3'-COOH and $H_2N$-A3-A2-A1-An(s)-A1'-A2'-A3'-COOH are polypeptides or proteins, wherein the mutation or non-mutation sites are either poorly recognized (owing to insignificant difference) or cannot be accessible (hidden) in its original nature form by antibody, and thus must be artificially, specifically and precisely created and/or exposed by residue chemical bond-specific hydrolysis in situ or ex situ in sample preparations; wherein $H_2N$— indicates the N-terminal direction and —COOH implies the C-terminal direction, wherein Am(s) is the mutated amino acid residue(s) that is different with the corresponding non-mutated amino acid residue(s) of An(s) in the non-mutation polypeptide/protein, wherein the covalent chemical bond(s) between Am(s) and its adjacent amino acid residues at either the N-terminal or C-terminal direction can be artificially, specifically and precisely cleaved by designed chemical bond-specific hydrolysis in samples and sample preparations to create (the new terminals) and/or expose said mutation-specific ACE structure for designing mutation-specific epitopes, making mutation-specific antibodies and for mutation-specific epitopes/antigens detection. Examples are given in FIGS. 1-7.

The ACE Antigen Design for Reducing Non-Specific Bindings.

The ACE methods can also be used to reduce antibody non-specific bindings in all antibody-based methods. The reduction of antibody non-specific binding is owing to the fact that the ACE methods can artificially, precisely and specifically create and/or expose the ACE, while breaking up the antibody non-specific binding structures.

2. Methods of Making Ace Antibodies.

The present invention further discloses methods of using ACE antigens to make ACE antibodies. Such antibodies can be made with ACE antigens in conjunction with all antibody making methods including but not limited to those described in the books: Antibodies—A Laboratory Manual (1988), Cold Spring Harbor Laboratory Press, and Current Protocols in Immunology (1997), John Wiley & Sons, Inc. Exemplary antibodies may be polyclonal, monoclonal, humanized, bispecific, heteroconjugate antibodies, antibody-like binding partners, and the like.

ACE Polyclonal Antibodies:

The ACE polyclonal antibody can usually be made by injecting specific ACE antigens into animals including, but not limited to, chickens, goats, guinea pigs, hamsters, horses, mice, rats, sheep and the like. Specific ACE haptens are usually linked to an immunogenic carrier including, but not limited to, KLH, serum albumin, bovine thyroglobulin, soybean trypsin inhibitor, or the like. Adjuvants are normally used to improve or enhance an immune response to antigens. Blood serum from these animals contains polyclonal antibodies, also known as antiserum, that bind to the same ACE hapten or antigen. Antigens may be also injected into chickens for generation of polyclonal antibodies in egg yolks.

ACE Monoclonal Antibodies:

The ACE monoclonal antibody is normally derived from a single cell line and obtained by fusing antibody-secreting lymphocytes with a cancer cell line. A mouse, hamster, rat, rabbit or other appropriate host animal can typically be immunized with a complete ACE antigen made by attaching an ACE hapten to an immunogenic carrier. Alternatively, the lymphocytes may be immunized in vitro. Spleen cells immunized with ACE antigens are then fused with myeloma cells using a fusing agent to make hybridomas. A mixture of hybridomas is then diluted and subcloned. The clones from single parent cells are then selected. The antibodies produced from the single clones (monoclonal) are then tested for their binding affinity and specificity to the antigens by any single or combinations of antibody-based methods including, but not limited to, immunoblotting, immunohistochemistry, immunocytochemistry, immunoprecipitation, flow cytometry, peptide array, ELISA or all other immunoassays, or immunoelectron microscopy. The clones with the highest binding affinity and specificity to the ACE structures or clones for specific applications are then selected and grown in cultures or in the peritoneal cavity of animals to a high volume for the production of monoclonal antibodies.

Antibodies can be purified using ACE hapten-conjugated matrices or resins, or by using Protein A/G or complete antigen-affinity chromatography for separation of antibodies from other molecules in crude antibody preparations. Negative absorptions may be required for separating mutation site-specific antibodies from the non-specific site.

ACE Recombinant Antibodies:

The ACE monoclonal antibodies may be natural or artificial (either partially or wholly), for example, recombinant DNA methods. Recombinant monoclonal antibody involves molecular cloning and expression of immunoglobulin gene segments in cells, viruses or yeasts. Immunoglobulin DNA expression vectors can be made with the DNAs from hybridoma cells immunized with ACE antigen. These vectors can then be transfected into a host cells including, but not limited to, myeloma cells in which recombinant monoclonal antibodies are expressed.

ACE Single-Domain Antibodies (Also Known as Single-Domain Antibody Fragments, Variable Domain of Heavy Chain Antibodies or VHHs, and Nanobodies):

Camelids and Cartilaginous fishes can produce a single N-terminal domain antibody (without the light chains). VHH is fully capable of antigen binding (Harmsen and De Haard, 2007). The expression vectors can be selected or cloned with ACE epitopes/antigens. The single-domain antibody fragments (VHHs) can be produced in microorganisms. VHHs can recognize hidden antigenic sites, and thus have advantage in detecting ACE epitopes/antigens. This ability is probably due to the smaller size and the ability of the extended CDR3 loop to penetrate into the ACE sites. Furthermore, VHHs are well suited for construction of bi-specific or multiple-specific ACE antibodies.

ACE Binding Partners:

The ACE antibodies or binding partners may also be made by methods including, but not limited to, phage display, yeast display, ribosome display, bacterial display, and mRNA display.

ACE Humanized Antibodies:

The ACE antigen can be used to make humanized antibodies or human antibodies made by recombinant methods. One approach is to merge an animal DNA sequence that encodes the small binding portion of a monoclonal antibody, with a human DNA sequence that encodes the rest of the large portion of the antibody. The hybrid DNA construct encoding the hybrid antibodies to ACE antigens can be readily isolated, sequenced and expressed for antibody production.

The feature of reducing nonspecific binding provides a further utility of the ACE methods. This is because chief obstacles associated with conventional antigen design and antibody production are: (i) weak antigenicity, (ii) antibody poor accessibility to antigen; and (iii) antibody non-specific binding. The inventive ACE methods can minimize all these obstacles by: (a) creating and/or exposing more antigenic N- and/or C-terminal ACE structure; (b) increasing antibody accessibility to the artificially and specifically created and/or exposed ACE structures; and (c) reducing non-specific bindings by the breakup of non-specific binding molecules.

The feature of reducing non-specific binding in the inventive methods may be also useful in immunoprecipitation (IP) studies. This is because the high levels of added immunoglobulin bands often disturb observing immuno-precipitated proteins/molecules of interest on Western blot membranes. The ACE methods can preserve the ACE structures while breaking up of added immunoglobulins on Western blot membranes, and thus eliminate unwanted immunoglobulin bands.

3. Methods of Ace Exposure and Detection.

The inventive ACE methods can solve the issues inherited in those epitopes that are: (i) hidden/concealed within molecule(s)/structure(s) and thus poorly or not recognizable, or not accessible to antibodies; (ii) poorly antigenic; and (iii) interfered with non-specific bindings. Such epitopes include, but are not limited to, those of protein mutation sites, those that are folded within their parent proteins/molecules, macromolecule-to-macromolecule covalent conjugation sites, molecule-to-molecule non-covalent binding sites, proteins/molecules that are inserted into cellular membranes, structures or organelles, and proteins/molecules that are interfered with non-specific bindings. In addition, the ACE structures with free terminals are more charged, and thus more antigenic than the internal sequence (Clark et al., 1969). Therefore, the ACE methods are effective in detecting hidden epitopes as shown in FIGS. 1-7.

In one embodiment, the invention provides methods of artificially, specifically and precisely creating and/or exposing ACE structures for detection; thus improving the ACE antigenicity and antibody accessibility in any types of sample preparations, wherein the ACE structures in samples or sample preparations are naturally absent or hidden, and poorly accessible to antibodies, and thus, must be artificially and precisely created and/or exposed either in sample preparations by specifically selected hydrolytic enzymes or agents; wherein the artificially creating and/or exposing the ACE structures can be carried out in any type of sample preparations including, but not limited to, in vivo or in vitro, in whole or part of biological bodies or organisms, in isolated organs or organelles, in tissues or tissue sections (with or without fixation), in isolated or cultured cells, in body fluids or cell culture media, in tissue or cell lysates, in cellular or subcellular fractions, on Western blot membranes, in chromatographic or centrifuge fractions, in biochemical assay mixtures, and the like.

The method of creating and exposing the ACE structure in a sample preparation further comprises treating the sample preparation with a fixative before treating the sample preparation with the hydrolytic enzyme or hydrolytic agent. The fixative is selected from the group consisting of an aldehyde, an alcohol, acetone, and osmium tetroxide, including, but not limited to, formaldehyde, paraformaldehyde, and glutaraldehyde.

The said hydrolytic enzymes and agents for artificial ACE creation and/or exposure are specific and precise, rather than random or accidental (also see below). The enzymes and agents should be mostly the same, but can also be very occasionally different, with the one(s) used for the ACE antigen design. If the different hydrolytic enzymes or agents are selected, they must preserve the ACE structures for detection. The availability, property and chemical bond specificity of hydrolytic enzymes and agents for ACE exposures and detections can be found in public disclosures, publications/literatures, and websites including, but not limited to: www.expasy.ch/tools/peptidecutter.

Other methods to improve the accessibility of a hidden epitope are to use detergents (such as Triton X100 or SDS), different pH solutions, or physical measures such as heat to treat sample before performing antibody-based detections. These methods are principally and profoundly different, and usually less, if any, effective, relative to the ACE detecting methods. One explanation is that detergent and heat treatments are non-specific, random or accidental, usually cannot break covalent chemical bonds near the mutation sites or folded molecules, and sometimes destroy (rather than expose) the epitopes. In comparison, the ACE methods employ the ACE antigen to make antibodies and then use ACE antigen design information to specifically, rather than randomly or accidentally, select residue chemical bond-specific hydrolytic enzyme(s)/agent(s) for artificially, specifically and precisely breaking the designated chemical bonds to create (new terminals) and/or expose the ACE structures for antibody detection. Therefore, the ACE methods not only fully preserve and expose the antigen structure, but also enhance antigenicity of the antigen structure by creating antigenic/charged terminals.

A number of antigen retrieval (AR) protocols have been published (Shi, 2011). To date, these protocols were solely for immunochemistry (ICC) or immunohistochemistry (IHC), and have been applied predominantly to archival "paraffin blocks" for IHC in diagnostic surgical pathology (Shi, 2011). Many antibody reagent companies also have antigen retrieval protocols on their websites. However, these protocols are not based on the ACE antigen design and detection described in this application, rather, they are based on random AR attempts and/or reversal of protein formaldehyde adducts and cross-links formed in the course of tissue fixation (Kuhlmann and Krischan, 1981). Therefore, these protocols are used solely for IHC or ICC and usually with a very low success rate, and have potential to destroy the antigen of interest. Therefore, the effectiveness of these protocols is accidental and unpredictable.

For example, most formalin-fixed tissue requires an antigen retrieval step before immunohistochemical staining can proceed. This is due to the formation of methylene bridges during fixation, which cross-link proteins and therefore mask antigenic sites." The Ihcworld's protocol (www.ihcworld.com) describes that "the use of enzyme digestion method may destroy some epitopes and tissue morphology". The protocol of R&D (www.rndsystems.com) recognizes that "the disadvantages of enzyme digestion method are the low success rate for restoring immunoreactivity and the potential for destroying both tissue morphology and the antigen of interest." It is also noted in the Millipore's protocol (www.millipore.com) that "the listed (enzyme digestion) procedure is only suggested; no warranty or guarantee of performance of the above procedure is made or implied".

For pathologists and morphologists, "seeing is believing" and most cancers are diagnosed by morphologic methods. O'Leary et al. (2010) and Shi (2011), two pioneers in the AR research, have suggested: "the AR technique is in many ways still in the developing stage. Further development of the AR technique must be based on a better scientific understanding of the molecular mechanisms, which represents the key pathways to improved cell/tissue sample preparation and standardization of IHC in clinical diagnostic applications."

The inventive ACE methods can robustly improve immunolabeling not only for IHC or ICC, but all antibody-based preparations including, but not limited to, in tissues or tissue lysates, cellular or subcellular fractions, Western blot membranes, chromatographic or centrifuge fractions, and the like.

An additional step of the ACE methods requires artificially, specifically and precisely create (terminals) and/or exposure of the ACE structure before detection. At first glance, this seems an additional step in compared with conventional antibody detection methods. However, in practice, this step can breakup non-specific binding molecules, thus reducing non-specific bindings significantly in all antibody-based applications.

Another issue may be that artificial creation of new terminals and/or exposure of the ACE structure may change the size of the protein/molecule to be detected. This obstacle can be overcome by separation of samples first by, for instance, Western blotting, followed by ACE structure exposure (in situ) on Western blot membranes with specifically selected hydrolytic enzyme(s) or agent(s) for detection. For immunohistochemistry, ACE in tissue sections can be exposed directly in situ with the specifically selected hydrolytic enzyme(s) or agent(s). After washing, the artificially exposed ACE structures can then be detected by the ACE antibody. For immunoassays, regular two-antibody sandwich methods can be used, i.e., a general antibody binds the non-mutation sites or the outside of the ACE structure, whereas the ACE antibody binds the mutation site ACE structures.

A host of residue chemical bond-specific hydrolytic enzymes or chemical agents including, but not limited to, proteases, glycosidases, lipases/phospholipases, poly(ADP-ribose) hydrolases, nucleases, and the likes, are available and can be specifically selected for the ACE methods. The criteria for selecting specific hydrolytic enzymes or agents for the ACE antigen design/detection depend on the molecular sequence of the ACE structure, and the substrate chemical bond-cleaving specificities, and the ACE organization, size and antigenicity. The selecting criteria also depend on which antibody-based methods/applications will be used. For Western blot analysis, for example, it is not ideal to select an enzyme that creates too small pieces of ACE structures. Therefore, the use of the ACE methods requires understanding the structure, organization and location information of hidden antigens, the properties of hydrolytic enzymes or chemical agents, and which antibody-based methods/applications are used.

4. Utilities of Ace Methods, Reagents, Antibodies, Immunoassays and Kits.

The present invention encompasses various utilities and applications of the ACE methods including, but not limited to: (i) research and discovery (R&D), (ii) diagnosing diseases, monitoring of disease stage and response to treatment, and disease prognosis, (iii) screening of therapeutic agents, (iv) determining mutation or non-mutation sites, (v) detecting hidden antigens that are normally difficult to be detected by general antibody-based methods, (vi) reducing antibody non-specific bindings in all antibody-based methods, and (vii) therapeutic applications for treatment of mutation-related diseases.

4.1. Diagnostic Applications of the ACE Methods, Antibodies, Reagents, Immunoassays and Kits:

Gene mutations occur in many diseases. However, mutation site-specific antibodies are difficult to make by the conventional antibody design and detecting methods. The inventive methods of designing and detecting mutation-specific or hidden ACE antigens can therefore be used for disease diagnosis, staging, monitoring progress and treatment, and prognosis, for example, diagnosis of cancers, diagnosis of neurological, neurodegenerative diseases, diagnosis of inherited diseases, and therapeutic antibodies.

4.2. Discovery of Mutation Sites and Sequences:

In bioreagent or R&D area, mutation-specific ACE methods, reagents, antibodies, immunoassays and kits can be used in all antibody-based applications including but not limited to detect, identify, isolation, locate and characterize protein mutation sites. The mutation-specific ACE structures can be artificially created and/or exposed directly either in situ or ex situ on Western blot membranes, tissue sections or any other type of biological sample preparations.

ACE methods, antibodies, reagents, immunoassays, and kits can be used directly for all antibody-based separations of mutation-specific ACE structures.

An example is to separate molecules in a biological sample with 2-dimensional electrophoresis gel, followed by exposing ACE structures with designated hydrolytic enzymes or agents, and then labeling the spots on the gel/blotting membranes with the ACE antibodies. The ACE positive spots on the gel or membrane can be cut, extracted, and identified with any mass spectrometry (MS)-related methods.

Another example is that ACE structures/segments can be captured with the ACE antibodies in a mixture or biological sample lysates, and then detected by any analytical methods. In the MS method, ACE parent macromolecules in a sample may need to be denatured, and then digested with designated hydrolytic enzymes or agents, to artificially, specifically and precisely expose the ACE structures. After isolation from the sample with the corresponding immobilized ACE antibodies, and then elution from antibody, the ACE structures can then be identified by MS-related methods.

An additional example is to identify ACE structures in samples by the method of antibody array-coupled peptide surface liquid extraction. The procedure includes: (i) coat ACE antibodies to surfaces or matrices mostly by covalent means; (ii) treat samples with specifically selected ACE hydrolytic enzymes or agents; (iii) inhibit the hydrolytic enzymes or agents with inhibitors or any other means, or separate the hydrolytic enzymes or agents from the samples by any biochemical means; (iv) incubate ACE segment-containing samples with ACE antibody-coated surfaces or matrices; (v) separate bound from non-bound ACE segments on the surfaces or matrices by washing; (vi) extract bound ACE segments by appropriate liquid including, but not limited to, low pH buffers or organic solvents; (vii) detect ACE segments in the liquid by any analytical means including, but not limited to, liquid chromatography, fluorescent, ultraviolet and visible spectrometry, or any MS-related methods.

5. Therapeutic Applications of the Ace Methods, Antibodies and Reagents.

The ACE antibodies of the invention may be useful, for example, in targeting the mutation sites, for treating mutation-related diseases including, but not limited to neurodegenerative diseases, cancer, vascular diseases, inflammatory diseases, macular degeneration, transplant rejection, multiple sclerosis, stroke, heart diseases, diabetes, infectious diseases and all protein mutation-related diseases.

The present invention may be relevant to the delivery of ACE antibodies to the target by carriers including, but not limited to, liposomes. This may be done by packing liposomes with mutation site-specific antibodies and hydrolytic enzymes including, but not limited to proteases, glycosidases/deglycosylases, lipases or phospholipases, nucleases, or cytotoxic agents such as chemotherapeutic agents, toxins, or radioactive isotopes. Review articles about immunoliposome and immunoliposome-mediated delivery can be found in publications (e.g., Pirollo et al., 2008; Brignole and Marimpietri et al., 2005; Bendas 2001; Maruyama, 2000).

The ACE antigen design of the invention may be used for preparations of vaccines to particular diseases including, but not limited to, cancers, neurodegenerative diseases, inherited diseases, and aging-related diseases. The vaccines may be preventive or therapeutic.

6. Kits

In another aspect, the present invention provides kits for detecting the ACEs in biological samples. Such kits comprise ACE antibodies, hydrolytic enzymes or agents, and other items including, but not limited to secondary antibodies, enzyme modulators, cofactors, and buffer systems.

REFERENCES CITED

Patent Documents

| | | |
|---|---|---|
| U.S. Pat. No. 7,491,501 | Feb. 17, 2009 | Wooten et al., (p62 as probe for protein ubiquitination) |
| U.S. Pat. No. 7,223,556 | May 29, 2007 | Zhou et al. (A method for targeting a target polypeptide for ubiquitin-dependent proteolysis) |
| US 20070218069A | Sep. 20, 2007 | Gordon et al. (about Polyubiquitin antibody) |
| US 20070037221 | Feb. 15, 2007 | Block et al. (Lectin-based diagnosis of liver cancer) |
| U.S. Pat. No. 7,022,493 | Apr. 4, 2006 | Issakani et al. (Ubiquitin conjugation assays) |
| U.S. Pat. No. 6,911,335 | Jun. 28, 2005 | Kapeller-Libermann et al. |
| U.S. Pat. No. 6,465,199 | Oct. 15, 2002 | Craig et al. (Compositions and methods for monitoring the modification of natural binding partners. This invention instead encompasses the use |

| | | |
|---|---|---|
| | | of FRET or other detection procedures to monitor the association of polypeptides). |
| U.S. Pat. No. 4,626,507 | Dec. 2, 1986 | Trowbridge et al. (Monoclonal antibody to a glycoprotein, but not specific to the glycosylation site) |
| U.S. Pat. No. 7,460,960 | Mar. 17, 2009 | Lee et al., Proteome epitope tags and methods of use thereof in protein modification analysis |
| WO 02/25287 | Mar. 4, 2003 | Soloviev et al., Detection of Peptide |
| U.S. Pat. No. 5,972,623 | Oct. 14, 1999 | Krane et al., Collagen-peptide assay method |
| U.S. Pat. No. 7,803,553 | Sep. 28, 2010 | Kojima et al., Methods of use of antibodies which recognize a protease cleavage site of an LAP fragment of TGF-β |
| U.S. Pat. No. 6,762,045 | Mar. 20, 2002 | Membrane derived caspase-3, compositions comprising the same and methods of use therefor |

OTHER REFERENCES

Kennedy S R, Loeb L A, Herr A J. Somatic mutations in aging, cancer and neurodegeneration. Mech Ageing Dev. 2012 April; 133(4):118-26.

Wood L D, Parsons D W, Jones S, Lin J, Sjöblom T, et al. The genomic landscapes of human breast and colorectal cancers. Science. 2007 Nov. 16; 318(5853):1108-13.

Wang Q, Chaerkady R, Wu J, Hwang H J, Papadopoulos N, Kopelovich L, Maitra A, Matthaei H, Eshleman J R, Hruban R H, Kinzler K W, Pandey A, Vogelstein B. Mutant proteins as cancer-specific biomarkers. Proc Natl Acad Sci USA. 2011 Feb. 8; 108(6):2444-9.

Neumann J, Zeindl-Eberhart E, Kirchner T, Jung A. Frequency and type of KRAS mutations in routine diagnostic analysis of metastatic colorectal cancer. Pathol Res Pract. 2009; 205(12):858-62.

Olivier M, Hollstein M, Hainaut P. TP53 Mutations in Human Cancers: Origins, Consequences, and Clinical Use. Cold Spring Harbor Perspectives in Biology. 2010; 2(1):a001008.

Harmsen M M, De Haard H J. Properties, production, and applications of camelid single-domain antibody fragments. Applied Microbiology and Biotechnology. 2007; 77(1):13-22.

Arnold J N, Saldova R, Hamid U M, Rudd P M (2008) Evaluation of the serum N-linked glycome for the diagnosis of cancer and chronic inflammation. Proteomics. 8:3284-3293.

Bendas G (2001) Immunoliposomes: A Promising Approach to Targeting Cancer Therapy. BioDrugs. 15:215-224.

Bian H, Grossman M. Frontotemporal lobar degeneration: recent progress in antemortem diagnosis. Acta Neuropathol. 2007, 114:23-9.

Block T M, Comunale M A, Lowman M, Steel L F, Romano P R, Fimmel C, Tennant B C, London W T, Evans A A, Blumberg B S, Dwek R A, Mattu T S, Mehta A S. Use of targeted glycoproteomics to identify serum glycoproteins that correlate with liver cancer in woodchucks and humans. Proc Natl Acad Sci USA. 2005, 102:779-84.

Breborowicz J, Mackiewicz A, Breborowicz D. Microheterogeneity of alpha-fetoprotein in patient serum as demonstrated by lectin affino-electrophoresis. Scand J Immunol. 1981, 14:15-20.

Brignole C, Marimpietri D, Pagnan G, Di Paolo D, Zancolli M, Pistoia V, Ponzoni M, Pastorino F. Neuroblastoma targeting by c-myb-selective antisense oligonucleotides entrapped in anti-GD2 immunoliposome: immune cell-mediated anti-tumor activities. Cancer Lett. 2005, 228: 181-6.

Bunkenborg J, Pilch B J, Podtelejnikov A V, Wiśniewski J R. Screening for N-glycosylated proteins by liquid chromatography mass spectrometry. Proteomics. 2004 4:454-65.

Cao J, Shen C, Wang H, Shen H, Chen Y, Nie A, Yan G, Lu H, Liu Y, Yang P. Identification of N-glycosylation sites on secreted proteins of human hepatocellular carcinoma cells with a complementary proteomics approach. J Proteome Res. 2009, 8:662-72.

Cardoso de Almeida M L, Turner M J. The membrane form of variant surface glycoproteins of *Trypanosoma brucei*. Nature. 1983, 302:349-52.

Chan C P, Cheung Y C, Renneberg R, Seydack M. New trends in immunoassays. Adv Biochem Eng Biotechnol. 2008, 109:123-54.

Chan M R, Shing M M, Poon T C, Johnson P J, Lam C W (2000) Alpha-fetoprotein variants in a case of pancreatoblastoma. Ann Clin Biochem. 37:681-685.

Clark L G, Maurer P H. Antigenicity of polypeptides (poly-alpha-amino acids). Immunological reactions of sheep antisera to a polymer of glutamic acid, alanine and tyrosine. Int Arch Allergy Appl Immunol. 1969, 35:58-64.

Comunale M A, Lowman M, Long R E, Krakover J, Philip R, Seeholzer S, Evans A A, Hann H W, Block T M, Mehta A S. Proteomic analysis of serum associated fucosylated glycoproteins in the development of primary hepatocellular carcinoma. J Proteome Res. 2006, 5:308-15.

Comunale M A, Wang M, Hafner J, Krakover J, Rodemich L, Kopenhaver B, Long R E, Junaidi O, Bisceglie A M, Block T M, Mehta A S. Identification and development of fucosylated glycoproteins as biomarkers of primary hepatocellular carcinoma. J Proteome Res. 2009, 8:595-602.

Cripps D, Thomas S N, Jeng Y, Yang F, Davies P, Yang A J, Alzheimer disease-specific conformation of hyperphosphorylated paired helical filament-Tau is polyubiquitinated through Lys-48, Lys-11, and Lys-6 ubiquitin conjugation. J Biol Chem. 2008, 281:10825-38.

de Leoz M L, An H J, Kronewitter S, Kim J, Beecroft S, Vinall R, Miyamoto S, de Vere White R, Lam K S, Lebrilla C. Glycomic approach for potential biomarkers on prostate cancer: profiling of N-linked glycans in human sera and pRNS cell lines. Dis Markers. 2008, 25:243-58.

Debruyne E N, Delanghe J R. Diagnosing and monitoring hepatocellular carcinoma with alpha-fetoprotein: new aspects and applications. Clin Chim Acta. 2008, 395:19-26.

Denis N J, Vasilescu J, Lambert J P, Smith J C, Figeys D (2007) Tryptic digestion of ubiquitin standards reveals an improved strategy for identifying ubiquitinated proteins by mass spectrometry. Proteomics. 7:868-874.

Dickson D W. Required techniques and useful molecular markers in the neuropathologic diagnosis of neurodegenerative diseases. Acta Neuropathol. 2005, 109:14-24.

Dohm C P, Kermer P, Bahr M (2008) Aggregopathy in neurodegenerative diseases: mechanisms and therapeutic implication. Neurodegener Dis. 5:321-38.

Durand G, Seta N (2000) Protein glycosylation and diseases: blood and urinary oligosaccharides as markers for diagnosis and therapeutic monitoring. Clin Chem. 46:795-805.

Engelender S. Ubiquitination of alpha-synuclein and autophagy in Parkinson's disease. Autophagy. 2008, 4:372-4.

Ferri N, Paoletti R, Corsini A. Lipid-modified proteins as biomarkers for cardiovascular disease: a review. Biomarkers. 2005, 10:219-37.

Finkbeiner S, Mitra S. The ubiquitin-proteasome pathway in Huntington's disease. Scientific World Journal. 2008, 8:421-33.

Fujimuro M, Yokosawa H. Production of antipolyubiquitin monoclonal antibodies and their use for characterization and isolation of polyubiquitinated proteins. Methods Enzymol. 2005; 399:75-86.

Gagné J P, Bonicalzi M E, Gagné P, Ouellet M E, Hendzel M J, Poirier G G. Poly(ADP-ribose) glycohydrolase is a component of the FMRP-associated messenger ribonucleoparticles. Biochem J. 2005, 392:499-509.

Goldfarb V, Trimble R B, De Falco M, Liem H H, Metcalfe S A, Wellner D, Muller-Eberhard U. An avian serum alpha 1-glycoprotein, hemopexin, differing significantly in both amino acid and carbohydrate composition from mammalian (beta-glycoprotein) counterparts. Biochemistry. 1986, 25:6555-62.

Gupta A K, Naregalkar R R, Vaidya V D, Gupta M. Recent advances on surface engineering of magnetic iron oxide nanoparticles and their biomedical applications. Nanomedicine (Lond), 2007, 2:23-39.

Hirabayashi J. Concept, strategy and realization of lectin-based glycan profiling. J Biochem. 2008, 144:139-47.

Hu P, Shi B, Geng F, Zhang C, Wu W, Wu X Z. E-cadherin core fucosylation regulates nuclear beta-catenin accumulation in lung cancer cells. Glycoconj J. 2008, 25:843-850.

Iwatsubo T, Yamaguchi H, Fujimuro M, Yokosawa H, Ihara Y, Trojanowski J Q, Lee V M. Purification and characterization of Lewy bodies from the brains of patients with diffuse Lewy body disease. Am J Pathol. 1996, 148:1517-29.

Jacob A L, Jordan B A, Weinberg R J. Organization of amyloid-beta protein precursor intracellular domain-associated protein-1 in the rat brain. J Comp Neurol. 2010, 518:3221-36.

Jellinger K A. Criteria for the neuropathological diagnosis of dementing disorders: routes out of the swamp? Acta Neuropathol. 2009, 117:101-10.

Kasai T, Tokuda T, Ishigami N, Sasayama H, Foulds P, Mitchell D J, Mann D M, Allsop D, Nakagawa M. Increased TDP-43 protein in cerebrospinal fluid of patients with amyotrophic lateral sclerosis. Acta Neuropathol. 2009, 117:55-62.

Kertesz V, Van Berkel G J. Fully automated liquid extraction-based surface sampling and ionization using a chip-based robotic nanoelectrospray platform. J Mass Spectrom. 2010, 45:252-60.

Kossowska B, Ferens-Sieczkowska M, Gancarz R, Passowicz-Muszyńska E, Jankowska R. Fucosylation of serum glycoproteins in lung cancer patients. Clin Chem Lab Med. 2005; 43:361-9.

Kudo T, Iqbal K, Ravid R, Swaab D F, Grundke-Iqbal I. Alzheimer disease: correlation of cerebro-spinal fluid and brain ubiquitin levels. Brain Res. 1994, 639:1-7.

Kuhlmann W D, Krischan R. Resin embedment of organs and postembedment localization of antigens by immunoperoxidase methods. Histochemistry. 1981, 72:377-89.

Li C, Simeone D M, Brenner D E, Anderson M A, Shedden K A, Ruffin M T, Lubman D M. Pancreatic cancer serum detection using a lectin/glyco-antibody array method. J Proteome Res. 2009, 8:483-92.

Li Y, Cozzi P J (2007) MUC1 is a promising therapeutic target for prostate cancer therapy. Curr Cancer Drug Targets. 7:259-271

Liang M, Liang Y Y, Wrighton K, Ungermannova D, Wang X P, Brunicardi F C, Liu X, Feng X H, Lin X (2004) Ubiquitination and proteolysis of cancer-derived Smad4 mutants by SCFSkp2. Mol Cell Biol. 24:7524-37.

Lobell R B, Omer C A, Abrams M T, Bhimnathwala H G, Brucker M J, Buser C A, Davide J P, deSolms S J, Dinsmore C J, Ellis-Hutchings M S, Kral A M, Liu D, Lumma W C, Machotka S V, Rands E, Williams T M, Graham S L, Hartman G D, Oliff A I, Heimbrook D C, Kohl N E. Evaluation of farnesyl:protein transferase and geranylgeranyl:protein transferase inhibitor combinations in preclinical models. Cancer Res. 2001, 61:8758-68.

Mai S, Garini Y (2006) The significance of telomeric aggregates in the interphase nuclei of tumor cells. J Cell Biochem. 97:904-915.

Maruyama K. In vivo targeting by liposomes. Biol Pharm Bull. 2000, 23:791-9.

Matsumoto K, Maeda Y, Kato S, Yuki H (1994) Alteration of asparagine-linked glycosylation in serum transferrin of patients with hepatocellular carcinoma. Clin Chim Acta. 224:1-8.

Matsumoto M L, Wertz I E, Kirkpatrick D S, Lill J R, Tan J, Dugger D, Gordon N, Sidhu S S, Fellouse F A, Komuves L, French D M, Ferrando R E, Lam C, Compaan D, Yu C, Bosanac I, Hymowitz S G, Kelley R F, Dixit V M. (2008) Ubiquitin chain editing revealed by polyubiquitin linkage-specific antibodies. Cell. 134:668-78.

Meerwaldt R, van der Vaart M G, van Dam G M, Tio R A, Hillebrands J L, Smit A J, Zeebregts C J (2008) Clinical relevance of advanced glycation endproducts for vascular surgery. Eur J Vasc Endovasc Surg. 36:125-31.

Mehta A, Block T M. Fucosylated glycoproteins as markers of liver disease. Dis Markers. 2008, 25:259-65.

Mehta A S, Long R E, Comunale M A, Wang M, Rodemich L, Krakover J, Philip R, Marrero J A, Dwek R A, Block T M (2008) Increased levels of galactose-deficient anti-Gal immunoglobulin G in the sera of hepatitis C virus-infected individuals with fibrosis and cirrhosis. J Virol. 82:1259-70.

Mehta P D, Thal L, Wisniewski H M, Grundke-Iqbal I, Iqbal K. Paired helical filament antigen in CSF. Lancet. 1985, 2:35.

Meray R K, Lansbury P T Jr. Reversible monoubiquitination regulates the Parkinson disease-associated ubiquitin hydrolase UCH-L1. J Biol Chem. 2007, 282:10567-10575

Miyoshi E, Shinzaki S, Moriwaki K, Matsumoto H (2010) Identification of fucosylated haptoglobin as a novel tumor marker for pancreatic cancer and its possible application for a clinical diagnostic test. Methods Enzymol. 478:153-64.

Moriwaki K, Miyoshi E (2010) Fucosylation and gastrointestinal cancer. World J Hepatol. 2:151-61.

Naitoh A, Aoyagi Y, Asakura H (1999) Highly enhanced fucosylation of serum glycoproteins in patients with hepatocellular carcinoma. J Gastroenterol Hepatol. 14:436-45.

Narisada M, Kawamoto S, Kuwamoto K, Moriwaki K, Nakagawa T, Matsumoto H, Asahi M, Koyama N, Miyoshi E (2008) Identification of an inducible factor secreted by pancreatic cancer cell lines that stimulates the production of fucosylated haptoglobin in hepatoma cells. Biochem Biophys Res Commun. 377:792-796.

O'Leary T J, Fowler C B, Evers D L, Cunningham R E, Mason J T. Commentary: future directions. In: Shi S-R, Taylor C R, editors. Antigen retrieval immunohistochemistry based research and diagnostics. Hoboken (N.J.): John Wiley. 2010, p. 323-331.

Osumi D, Takahashi M, Miyoshi E, Yokoe S, Lee S H, Noda K, Nakamori S, Gu J, Ikeda Y, Kuroki Y, Sengoku K, Ishikawa M, Taniguchi N. Core fucosylation of E-cadherin enhances cell-cell adhesion in human colon carcinoma WiDr cells. Cancer Sci. 2009, 100:888-95.

Otake Y, Fujimoto I, Tanaka F, Nakagawa T, Ikeda T, Menon K K, Hase S, Wada H, Ikenaka K (2001) Isolation and characterization of an N-linked oligosaccharide that is significantly increased in sera from patients with non-small cell lung cancer. J Biochem. 129:537-42.

Parsons R B, Farrant J K, Price G C, Subramaniam D, Austen B M. Regulation of the lipidation of beta-secretase by statins. Biochem Soc Trans. 2007, 35:577-82.

Peng J, Schwartz D, Elias J E, Thoreen C C, Cheng D, Marsischky G, Roelofs J, Finley D and Gygi S P (2003) A proteomics approach to understanding protein ubiquitination. Nat Biotechnol. 21:921-926.

Perry G, Mulvihill P, Fried V A, Smith H T, Grundke-Iqbal I, Iqbal K. Immunochemical properties of ubiquitin conjugates in the paired helical filaments of Alzheimer disease. J Neurochem. 1989, 52:1523-8.

Pirim I (1998) Production of anti-polyubiquitin and anti-ubiquitin carboxyl terminal hydrolase antibodies and immunohistochemically assessment of them on brain sections of Alzheimer's disease and Lewy body disease. Int J Neurosci. 95:33-42.

Pirollo K F, Chang E H. Targeted delivery of small interfering RNA: approaching effective cancer therapies. Cancer Res. 2008, 68:1247-50.

Ressom H W, Varghese R S, Goldman L, An Y, Loffredo C A, Abdel-Hamid M, Kyselova Z, Mechref Y, Novotny M, Drake S K, Goldman R. Analysis of MALDI-TOF mass spectrometry data for discovery of peptide and glycan biomarkers of hepatocellular carcinoma. J Proteome Res. 2008, 7:603-10.

Saffroy R, Pham P, Reffas M, Takka M, Lemoine A, Debuire B (2007) New perspectives and strategy research biomarkers for hepatocellular carcinoma. Clin Chem Lab Med. 45:1169-1179.

Saldova R, Fan Y, Fitzpatrick J M, Watson R W, Rudd P M (2010) Core fucosylation and {alpha}2-3 sialylation in serum N-glycome is significantly increased in prostate cancer comparing to benign prostate hyperplasia. Glycobiology. [Epub ahead of print]

Sato S, Johnson W (2007) Antibody-mediated neutralization and simian immunodeficiency virus models of HIV/AIDS. Curr HIV Res. 5:594-607.

Sekine C, Aoyagi Y, Suzuki Y, Ichida F. The reactivity of alpha-1-antitrypsin with Lens culinaris agglutinin and its usefulness in the diagnosis of neoplastic diseases of the liver. Br J Cancer. 1987, 56:371-5.

Shi S R, Shi Y, Taylor C R. Antigen retrieval immunohistochemistry: review and future prospects in research and diagnosis over two decades. J Histochem Cytochem. 2011, 59:13-32.

Sou Y S, Tanida I, Komatsu M, Ueno T, Kominami E. Phosphatidylserine in addition to phosphatidylethanolamine is an in vitro target of the mammalian Atg8 modifiers, LC3, GABARAP, and GATE-16. J Biol Chem. 2006, 281:3017-24.

Steffan J S, Agrawal N, Pallos J, Rockabrand E, Trotman L C, Slepko N, Illes K, Lukacsovich T, Zhu Y Z, Cattaneo E, Pandolfi P P, Thompson L M, Marsh J L. SUMO modification of Huntingtin and Huntington's disease pathology. Science. 2004, 304:100-4.

Steinacker P, Hendrich C, Sperfeld A D, Jesse S, von Arnim C A, Lehnert S, Pabst A, Uttner I, Tumani H, Lee V M, Trojanowski J Q, Kretzschmar H A, Ludolph A, Neumann M, Otto M. TDP-43 in cerebrospinal fluid of patients with frontotemporal lobar degeneration and amyotrophic lateral sclerosis. Arch Neurol. 2008, 65:1481-7.

Sturla L, Fruscione F, Noda K, Miyoshi E, Taniguchi N, Contini P, Tonetti M. Core fucosylation of N-linked glycans in leukocyte adhesion deficiency/congenital disorder of glycosylation IIc fibroblasts. Glycobiology. 2005, 15:924-34.

Szargel R, Rott R, Engelender S. Synphilin-1 isoforms in Parkinson's disease: regulation by phosphorylation and ubiquitylation. Cell Mol Life Sci. 2008, 65:80-8.

Thornalley P J (2002) Glycation in diabetic neuropathy: characteristics, consequences, causes, and therapeutic options. Int Rev Neurobiol. 50:37-57.

Tong L, Baskaran G, Jones M B, Rhee J K, Yarema K J (2003) Glycosylation changes as markers for the diagnosis and treatment of human disease. Biotechnol Genet Eng Rev. 20:199-244.

Troyer D A, Mubiru J, Leach R J, Naylor S L (2004) Promise and challenge: Markers of prostate cancer detection, diagnosis and prognosis. Dis Markers. 20:117-128

Valmu L, Alfthan H, Hotakainen K, Birken S, Stenman U H. Site-specific glycan analysis of human chorionic gonadotropin beta-subunit from malignancies and pregnancy by liquid chromatography—electrospray mass spectrometry. Glycobiology. 2006, 16:1207-18.

Waelter S, Boeddrich A, Lurz R, Scherzinger E, Lueder G, Lehrach H, Wanker E E. Accumulation of mutant huntingtin fragments in aggresome-like inclusion bodies as a result of insufficient protein degradation. Mol Biol Cell. 2001, 12:1393-1407.

Wang H, Matsuzawa A, Brown S A, Zhou J, Guy C S, Tseng P H, Forbes K, Nicholson T P, Sheppard P W, Hacker H, Karin M, Vignali D A. Analysis of nondegradative protein ubiquitylation with a monoclonal antibody specific for lysine-63-linked polyubiquitin. Proc Natl Acad Sci USA. 2008, 105:20197-202.

Wang X, Gu J, Miyoshi E, Honke K, Taniguchi N. Phenotype changes of Fut8 knockout mouse: core fucosylation is crucial for the function of growth factor receptor(s). Methods Enzymol. 2006, 417:11-22.

Ward R (2002) Antibody phage display. Immunology and Cell Biology. 80:316-317,

White K Y, Rodemich L, Nyalwidhe J O, Comunale M A, Clements M A, Lance R S, Schellhammer P F, Mehta A S, Semmes O J, Drake R R. Glycomic characterization of prostate-specific antigen and prostatic acid phosphatase in prostate cancer and benign disease seminal plasma fluids. J Proteome Res. 2009, 8:620-30.

Wu L H, Shi B Z, Zhao Q L, Wu X Z (2010) Fucosylated glycan inhibition of human hepatocellular carcinoma cell migration through binding to chemokine receptors. Glycobiology. 20:215-23.

Xu G, Paige J S and Jaffrey S R (2010) Global analysis of lysine ubiquitination by ubiquitin remnant immunoaffinity profiling. Nat Biotechnol. 28:868-73.

Yamashita K, Koide N, Endo T, Iwaki Y, Kobata A. Altered glycosylation of serum transferrin of patients with hepatocellular carcinoma. J Biol Chem. 1989, 264:2415-23.

Yang W, Sheng H, Warner D S, Paschen W. Transient global cerebral_ischemia induces a massive increase in protein sumoylation. J Cereb Blood Flow Metab. 2008, 28:269-279.

Young L S, Gascon R, Alam S, Bermudez L E. Monoclonal antibodies for treatment of gram-negative infections. Rev Infect Dis. 1989 November-December; 11 Suppl 7:S1564-71.

Zhao J, Patwa T H, Lubman D M, Simeone D M (2008) Protein biomarkers in cancer: natural glycoprotein microarray approaches. Curr Opin Mol Ther. 10:602-610.

We claim:

1. A method of detecting a mutation-specific or non-mutation-specific hydrolysis-created Artificially Cleaved Epitope (ACE) structure in a sample, wherein the ACE structure is present only in either a mutant form or the non-mutant form, comprising steps of:
   (i) designing an ACE structure derived from a basic mutation-specific structure H2N-A3-A2-A1-Am(s)-A1'-A2'-A3'-COOH, or a basic non-mutation-specific structure H2N-A3-A2-A1-An(s)-A1'-A2'-A3'-COOH, wherein A1, A2, A3, Am(s) or An(s), A1', A2' and A3' are amino acid residue(s) of a polypeptide/protein, wherein Am(s) is the mutated amino acid residue(s) that is different with the corresponding non-mutated amino acid residue(s) or An(s), wherein the peptide bond(s) between Am(s) or An(s) and its adjacent amino acid residues is artificially cleaved via chemical bond-specific hydrolytic enzyme or agent, and wherein the antibody specifically recognizes at least the Am(s) or An(s) residue(s);
   (ii) synthesizing the ACE structure;
   (iii) making an antibody against the ACE structure;
   (iv) creating the ACE structure in the sample by treating the sample preparation with the hydrolytic enzyme or hydrolytic agent, thereby exposing the formerly less antigenic or hidden ACE structure to specific interaction with the antibody; and
   (v) detecting the ACE structure created in step (iv) with the antibody, wherein the antibody specifically binds to at least one of the artificially created Am(s) or An(s) residue(s).

2. The method of claim 1 wherein the antibody is a polyclonal antibody, a monoclonal antibody, a bi-specific antibody, a recombinant antibody, a humanized antibody, a single chain or single domain antibody, an antibody fragment, or an antibody-like molecule.

3. The method of claim 1 wherein the hydrolytic enzyme is selected from the group consisting of a protease, a glycosidase, a lipase, a phospholipase, a nuclease, a polyribosyl hydrolase, and their combinations.

4. The method of claim 1 wherein the hydrolytic agent(s) is selected from a substance with chemical bond-specific hydrolysis activity.

5. The hydrolytic agents of claim 4 wherein the hydrolytic agents are BNPS-skatole (3-bromo-3-methyl-2-[(2-nitrophenyl)thio]-3H-indole), CNBr (cyanogen bromide), formic acid, hydroxylamine (NH2OH), iodosobenzoic acid, and NTCB+Ni (2-nitro-5-thiocyanobenzoic acid).

6. The method of claim 1 wherein the sample preparation is selected from the group consisting of a blot membrane, a tissue section, an isolated organ, an isolated cell, an isolated organelle, isolated tissue, an isolated body fluid, cell culture media, cell lysate, tissue lysate, an isolated fraction, a subcellular fraction, a chromatographic fraction, an immunocomplex, and a centrifuge fraction.

7. The method of claim 1 wherein the step of synthesizing the ACE structure further comprises treating the synthesized ACE structure with a fixative.

8. The method of claim 7 wherein the fixative is selected from the group consisting of an aldehyde, an alcohol, acetone, and osmium tetroxide.

9. A method of detecting a mutation-specific or non-mutation-specific hydrolysis-created Artificially Cleaved Epitope (ACE) structure in a sample, wherein the ACE structure is present only in either a mutant form or the non-mutant form, comprising steps of:
   (i) designing an ACE structure derived from a basic mutation-specific structure H2N-A3-A2-A1-Am(s)-A1'-A2'-A3'-COOH, or a basic non-mutation-specific structure H2N-A3-A2-A1-An(s)-A1'-A2'-A3'-COOH, wherein A1, A2, A3, Am(s) or An(s), A1', A2' and A3' are amino acid residue(s) of a polypeptide/protein, wherein Am(s) is the mutated amino acid residue(s) that is different with the corresponding non-mutated amino acid residue(s) or An(s), wherein the peptide bond(s) between Am(s) or An(s) and its adjacent amino acid residues is artificially cleaved via chemical bond-specific hydrolytic enzyme selected from the group consisting of a protease, a glycosidase, a lipase, a phospholipase, a nuclease, a polyribosyl hydrolase, and their combinations or hydrolytic agent selected from a substance with chemical bond-specific hydrolysis activity, and wherein the antibody specifically recognizes at least the Am(s) or An(s) residue(s);
   (ii) synthesizing the ACE structure;
   (iii) making an antibody against the ACE structure, wherein the antibody is a polyclonal antibody, a monoclonal antibody, a bi-specific antibody, a recombinant antibody, a humanized antibody, a single chain or single domain antibody, an antibody fragment, or an antibody-like molecule;
   (iv) creating the ACE structure in a sample by treating the sample preparation with the hydrolytic enzyme or hydrolytic agent, thereby exposing the formerly less antigenic or hidden ACE structure to specific interaction with the antibody; and
   (v) detecting the ACE structure created in step (iv) with the antibody, wherein the antibody specifically binds to at least one of the artificially created Am(s) or An(s) residue(s).

10. The method of claim 9 wherein the sample preparation is selected from the group consisting of a blot membrane, a tissue section, an isolated organ, an isolated cell, an isolated organelle, isolated tissue, an isolated body fluid, cell culture media, cell lysate, tissue lysate, an isolated fraction, a subcellular fraction, a chromatographic fraction, an immunocomplex, and a centrifuge fraction.

* * * * *